US011845813B2

(12) United States Patent
Grobe, III et al.

(10) Patent No.: US 11,845,813 B2
(45) Date of Patent: Dec. 19, 2023

(54) CROSSLINKED POLYMERIC NETWORK AND USE THEREOF

(71) Applicant: Bausch & Lomb Incorporated, Rochester, NY (US)

(72) Inventors: George L Grobe, III, Ontario, NY (US); Alok Kumar Awasthi, Pittsford, NY (US); Mark R. Mis, Rush, NY (US); Jennah L. Wolcott, Perry, NY (US); James R. Hauenstein, Williamson, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 56 days.

(21) Appl. No.: 17/845,038

(22) Filed: Jun. 21, 2022

(65) Prior Publication Data
US 2022/0325006 A1 Oct. 13, 2022

Related U.S. Application Data

(62) Division of application No. 17/533,454, filed on Nov. 23, 2021, now Pat. No. 11,421,047, which is a division of application No. 16/739,547, filed on Jan. 10, 2020, now Pat. No. 11,732,060.

(60) Provisional application No. 62/798,668, filed on Jan. 30, 2019.

(51) Int. Cl.
| C08B 37/00 | (2006.01) |
| A45C 11/00 | (2006.01) |
| A61K 9/00 | (2006.01) |
| A61K 31/726 | (2006.01) |
| A61K 31/728 | (2006.01) |
| A61L 26/00 | (2006.01) |
| A61L 27/34 | (2006.01) |
| C08B 37/08 | (2006.01) |
| G02C 7/04 | (2006.01) |

(52) U.S. Cl.
CPC ........ *C08B 37/0069* (2013.01); *A45C 11/005* (2013.01); *A61K 9/0048* (2013.01); *A61K 31/726* (2013.01); *A61K 31/728* (2013.01); *A61L 26/0023* (2013.01); *A61L 27/34* (2013.01); *C08B 37/0072* (2013.01); *G02C 7/049* (2013.01)

(58) Field of Classification Search
None
See application file for complete search history.

(56) References Cited

U.S. PATENT DOCUMENTS

| 3,408,429 A | 10/1968 | Wichterle |
| 3,660,545 A | 5/1972 | Wichterle |
| 4,113,224 A | 9/1978 | Clark et al. |
| 4,136,250 A | 1/1979 | Mueller et al. |
| 4,143,949 A | 3/1979 | Chen |
| 4,153,641 A | 5/1979 | Deichert et al. |
| 4,197,266 A | 4/1980 | Clark et al. |
| 4,312,575 A | 1/1982 | Peyman et al. |
| 4,555,732 A | 11/1985 | Tuhro |
| 4,740,533 A | 4/1988 | Su et al. |
| 4,758,595 A | 7/1988 | Ogunbiyi et al. |
| 4,954,587 A | 9/1990 | Mueller |
| 5,010,141 A | 4/1991 | Mueller |
| 5,034,461 A | 7/1991 | Lai et al. |
| 5,070,215 A | 12/1991 | Bambury et al. |
| 5,079,319 A | 1/1992 | Mueller |
| 5,260,000 A | 11/1993 | Nandu et al. |
| 5,271,876 A | 12/1993 | Ibar |
| 5,310,779 A | 5/1994 | Lai |
| 5,321,108 A | 6/1994 | Kunzler et al. |
| 5,358,995 A | 10/1994 | Lai et al. |
| 5,387,662 A | 2/1995 | Kunzler et al. |
| 5,449,729 A | 9/1995 | Lai |
| 5,464,667 A | 11/1995 | Kohler et al. |
| 5,512,205 A | 4/1996 | Lai |
| 5,573,726 A | 11/1996 | Dassanayake et al. |
| 5,610,252 A | 3/1997 | Bambury et al. |
| 5,616,757 A | 4/1997 | Bambury et al. |
| 5,708,094 A | 1/1998 | Lai et al. |

(Continued)

FOREIGN PATENT DOCUMENTS

| CN | 1075970 A | 9/1993 |
| CN | 101502675 A | 8/2009 |

(Continued)

OTHER PUBLICATIONS

Lai, Yu-Chin, "The Role of Bulky Polysiloxanylalkyl Methacryates in Polyurethane-Polysiloxane Hydrogels," Journal of Applied Polymer Science, 1996, pp. 1193-1199, vol. 60.

Marjorie J. Rah, "A Review of hyaluronan and its ophthalmic applications," Optometry, 2011, pp. 38-43, vol. 82.

A. Sannino et al., "Cellulose Derivative-Hyaluronic Acid-Based Microporous Hydrogels Cross-Linked through Divinyl Sulfone (DVS) To Modulate Equilibrium Sorption Capacity and Network Stability," Biomacromolecules, 2004, pp. 92-96, vol. 5.

Eun Ju Oh et al., "Control of the Molecular degradation of hyaluronic acid hydrogels for tissue augmentation," Journal of Biomedical Materials Research Part A, 2007, pp. 687-693.

M. Sundrarajan et al., "Dyeing of Sulfonation and Crosslinked Cotton Fabric", Autex Research Journal, Jun. 2009, pp. 71-77, vol. 9, No. 2.

(Continued)

*Primary Examiner* — Layla D Berry

(74) *Attorney, Agent, or Firm* — Ryan, Mason & Lewis, LLP

(57) ABSTRACT

A packaging system for the storage of an ophthalmic device includes a sealed container containing one or more unused ophthalmic devices immersed in an aqueous packaging solution comprising one or more crosslinked polymeric networks. The one or more crosslinked polymeric network comprises a reaction product of a first glycosaminoglycan, a second glycosaminoglycan, and a first crosslinking agent, wherein the first glycosaminoglycan is different than the second glycosaminoglycan. The aqueous packaging solution has an osmolality of at least about 180 mOsm/kg, a pH of about 6 to about 9 and is heat sterilized.

20 Claims, No Drawings

(56) References Cited

U.S. PATENT DOCUMENTS

| | | |
|---|---|---|
| 5,710,302 A | 1/1998 | Kunzler et al. |
| 5,714,557 A | 2/1998 | Kunzler et al. |
| 5,731,298 A | 3/1998 | Reinmuller |
| 5,908,906 A | 6/1999 | Kunzler et al. |
| 6,075,066 A | 6/2000 | Matsuda et al. |
| 7,928,069 B2 | 4/2011 | Prestwich et al. |
| 7,981,871 B2 | 7/2011 | Prestwich et al. |
| 7,994,356 B2 | 8/2011 | Awasthi et al. |
| 8,329,673 B2 | 12/2012 | Prestwich et al. |
| 8,343,942 B2 | 1/2013 | Oottamasathien et al. |
| 8,691,793 B2 | 4/2014 | Prestwich et al. |
| 8,859,523 B2 | 10/2014 | Prestwich et al. |
| 2007/0293648 A1 | 12/2007 | Sheardown et al. |
| 2008/0141628 A1 | 6/2008 | Lang et al. |
| 2010/0086512 A1 | 4/2010 | Schaefer |
| 2010/0178317 A1 | 7/2010 | Burke et al. |
| 2011/0077737 A1 | 3/2011 | Stroumpoulis et al. |
| 2012/0269862 A1 | 10/2012 | Chowhan et al. |
| 2017/0143870 A1 | 5/2017 | Linko et al. |

FOREIGN PATENT DOCUMENTS

| | | | |
|---|---|---|---|
| CN | 101721349 A | 7/2011 | |
| CN | 104220078 A | 12/2014 | |
| CN | 102911380 A | 3/2015 | |
| CN | 104225677 A | 9/2016 | |
| CN | 202080009811.1 | 8/2022 | |
| EP | 0554898 A1 | 8/1993 | |
| EP | 2011816 A1 | 1/2009 | |
| EP | 2171025 B1 * | 4/2012 | ........... A61L 12/142 |
| EP | 3187510 A1 | 7/2017 | |
| WO | 8906964 A1 | 8/1989 | |
| WO | 9406485 A1 | 3/1994 | |
| WO | 9631792 A1 | 10/1996 | |
| WO | 02/06373 A1 | 1/2002 | |
| WO | 2010145821 A1 | 12/2010 | |
| WO | 2015149941 A1 | 10/2015 | |

OTHER PUBLICATIONS

Kristoffer Bergman et al., Hyaloronic Acid Derivatives Prepared in Aqueous Media by Triazine-Actived Amidation, 2007, pp. 2190-2195, vol. 8.

Carole E. Schante et al., "Improvement of hyaluronic acid enzymatic stability by the grafting of amino-acids", Carbohydrate Polymers, 2012, pp. 2211-2216, vol. 87.

Nobuhiko Yui et al., "Inflammation responsive degradation of crosslinked hyaluronic acid gels," Journal of Controlled Release, 1992, pp. 105-116, vol. 22.

Qiang Li et al., "Photocrosslinkable polysaccharides based on chondroitin sulfate," Wiley Periodicals, Inc., 2003, pp. 28-33.

Yuko Inoue et al., "Preparation, By Chemical Degradation of Hyaluronic Acid, of a Series of Even- and Odd-Numbered Oligosaccharides having a 2-acetamido-2-deoxy-D-glucose and a D-glucoronic acid residue, respectively, at the reducing end", Carbohydrate Research, 1985, pp. 99-110, vol. 141.

Jing Yu et al., "The Boundary Lubrication of Chemically Grafted and Cross-Linked Hyaluronic Acid in Phosphate Buffered Saline and Lipid Solutions Measured by the Surface Forces Apparatus", Langmuir, 2012, pp. 2244-2250, vol. 28.

Fu et al., "Injectable hyaluronic acid/ poly( ethylene glycol) hydrogels crosslinked via strain-promoted azide-alkyne cycloaddition click reaction," Carbohydrate Polymers, 2017, 169, pp. 332-340.

Jinghua et al., "Research of Cross-Linking Reagent For Producing Hyaluronic Acid Derivative", Chinese J. Reparative and Reconstructive Surgery, Jan. 15, 2004, pp. 74-77, vol. 18(1).

* cited by examiner

CROSSLINKED POLYMERIC NETWORK AND USE THEREOF

PRIORITY CLAIM

The present application is a divisional application of U.S. Ser. No. 17/533,454, filed Nov. 23, 2021, now issued as U.S. Pat. No. 11,421,047, which is a divisional application of U.S. Ser. No. 16/739,547, filed Jan. 10, 2020, now issued as U.S. Pat. No. 11,732,060, which claims priority to U.S. Provisional Patent Application Ser. No. 62/798,668, filed Jan. 30, 2019, and entitled "Crosslinked Polymeric Network and Use Thereof," the contents of each being incorporated by reference herein in their entirety.

BACKGROUND

The present invention generally relates to a crosslinked polymer network and its use.

It is highly desirable that a contact lens be as comfortable as possible for wearers. Manufacturers of contact lenses are continually working to improve the comfort of the lenses. Nevertheless, many people who wear contact lenses still experience dryness or eye irritation throughout the day and particularly towards the end of the day. An insufficiently wetted lens at any point in time will cause significant discomfort to the lens wearer. Although wetting drops can be used as needed to alleviate such discomfort, it would certainly be desirable if such discomfort did not arise in the first place.

Glycosaminoglycans (GAGs) are a group of polysaccharides built of repeating disaccharide units. Due to high polarity and water affinity, they can be found in many systems of human bodies. For example, GAGs occur on the surface of cells and in the extracellular matrix of animal organisms such as skin, cartilage, and lungs.

GAGs each have a chemical structure including a repeating basal disaccharide structure consisting of uronic acid and hexosamine and being optionally sulfated to various degrees. GAGs are mainly classified, depending on the disaccharides constituting them, into three groups: a first group of compounds composed of chondroitin sulfate or dermatan sulfate, a second group of compounds composed of heparan sulfate or heparin, and a third group of hyaluronic acid compounds. For example, the compounds composed of chondroitin sulfate or dermatan sulfate consist of a disaccharide:uronic acid (glucuronic acid or iduronic acid) ($\beta 1 \rightarrow 3$) N-acetylgalactosamine, the compounds composed of heparan sulfate or heparin consist of a disaccharide:uronic acid (glucuronic acid or iduronic acid) ($\beta 1 \rightarrow 4$) N-acetylglucosamine, and the hyaluronic acid consists of a disaccharide:glucuronic acid ($\beta 1 \rightarrow 3$) N-acetylglucosamine. In addition, the structure is highly diverse due to a combination with modification by sulfation.

These GAGs are known as important biological materials having both physicochemical properties derived from characteristic viscoelasticity and biological properties mediated by interactions with various functional proteins, depending on the molecular size and the sulfation pattern.

It would be desirable to provide improved GAGs that can make a biomedical device such as a contact lens as comfortable as possible for the wearer and exhibit suitable physical and chemical properties, e.g., lubriciousness and wettability.

SUMMARY

In accordance with one embodiment of the present invention, a crosslinked polymeric network is provided comprising a reaction product of a first glycosaminoglycan, a second glycosaminoglycan, and one or more crosslinking agents, wherein the first glycosaminoglycan is different than the second glycosaminoglycan.

In accordance with a second embodiment of the present invention, a crosslinked polymeric network is provided comprising a first glycosaminoglycan crosslinked with a second glycosaminoglycan, wherein the first glycosaminoglycan is different than the second glycosaminoglycan.

In accordance with a third embodiment of the present invention, a biomedical device having a coating on a surface thereof is provided, the coating comprising one or more crosslinked polymeric networks comprising a reaction product of a first glycosaminoglycan, a second glycosaminoglycan, and one or more crosslinking agents, wherein the first glycosaminoglycan is different than the second glycosaminoglycan.

In accordance with a fourth embodiment of the present invention, a packaging system for the storage of an ophthalmic device is provided comprising a sealed container containing one or more unused ophthalmic devices immersed in an aqueous packaging solution comprising one or more crosslinked polymeric networks comprising a reaction product of a first glycosaminoglycan, a second glycosaminoglycan, and one or more crosslinking agents, wherein the first glycosaminoglycan is different than the second glycosaminoglycan, wherein the solution has an osmolality of at least about 200 mOsm/kg, a pH of about 6 to about 9 and is heat sterilized.

In accordance with a fifth embodiment of the present invention, a method of preparing a package comprising a storable, sterile ophthalmic device is provided, the method comprising: (a) immersing an ophthalmic device in an aqueous packaging solution comprising one or more crosslinked polymeric networks comprising a reaction product of a first glycosaminoglycan, a second glycosaminoglycan, and one or more crosslinking agents, wherein the first glycosaminoglycan is different than the second glycosaminoglycan, wherein the solution has an osmolality of at least about 200 mOsm/kg and a pH in the range of about 6 to about 9; (b) packaging the solution and the device in a manner preventing contamination of the device by microorganisms; and (c) sterilizing the packaged solution and device.

In accordance with a sixth embodiment of the present invention, an aqueous ophthalmic composition is provided comprising one or more crosslinked polymeric networks comprising a reaction product of a first glycosaminoglycan, a second glycosaminoglycan, and one or more crosslinking agents, wherein the first glycosaminoglycan is different than the second glycosaminoglycan, wherein the aqueous ophthalmic composition has an osmolality in a range from 200 mOsmol/kg to 400 mOsmol/kg.

In accordance with a seventh embodiment of the present invention, a gel composition for promoting wound healing is provided wherein the gel composition comprises one or more crosslinked polymeric networks comprising a reaction product of a first glycosaminoglycan, a second glycosaminoglycan, and one or more crosslinking agents, wherein the first glycosaminoglycan is different than the second glycosaminoglycan.

In accordance with an eighth embodiment of the present invention, a wound dressing is provided comprising a gel composition comprising one or more crosslinked polymeric networks comprising a reaction product of a first glycosaminoglycan, a second glycosaminoglycan, and one or more crosslinking agents, wherein the first glycosaminoglycan is different than the second glycosaminoglycan.

The crosslinked polymeric networks of the present invention advantageously exhibit suitable physical and chemical properties, e.g., oxygen permeability, lubriciousness mucoadhesivity and wettability, for prolonged contact with the body by crosslinking a first glycosaminoglycan with a second glycosaminoglycan, wherein the first glycosaminoglycan is different than the second glycosaminoglycan. The crosslinked polymeric networks of the present invention advantageously provide improved lubricty to the surface of a biomedical device such as a contact lens. For example, the benefits of improved lubricity using the crosslinked polymeric networks of the present invention include, for example, minimizing interactions between a contact lens and its respective packaging blister, a lens surface that is more robust toward processing and handling conditions, and improved comfort upon insertion into a subject's eye, as well as reduced deposition (e.g., protein, lipid) and thus potentially reducing biofilm formation by the contact lens wearer onto the lens surface.

In addition, the crosslinked polymeric networks of the present invention advantageously provide improved wettability to the surface of a biomedical device such as a contact lens. It is believed that the benefits of having improved wettability using the crosslinked polymeric networks of the present invention include, for example, delaying evaporation of the aqueous layer of the device due to its effect like-coating on the ocular surface and moisturizing properties and thus potentially relieving dry eye symptoms.

DETAILED DESCRIPTION

The illustrative embodiments described herein are directed to a crosslinked polymeric network useful in treating the surface of a biomedical device intended for direct contact with body tissue or fluid. In general, the crosslinked polymeric network comprises a reaction product of a first glycosaminoglycan (GAG), a second glycosaminoglycan, and one or more crosslinking agents, wherein the first glycosaminoglycan is different than the second glycosaminoglycan. A GAG is one molecule with many alternating subunits. In general, GAGs are represented by the formula A-B-A-B-A-B, where A is an uronic acid and B is an amino sugar that is either O- or N-sulfated, where the A and B units can be heterogeneous with respect to epimeric content or sulfation. Any natural or synthetic polymer containing uronic acid can be used. Other GAGs are sulfated at different sugars. There are many different types of GAGs having commonly understood structures such as, for example, chondroitin sulfate, dermatan, heparan, heparin, dermatan sulfate, hyaluronic acid or a salt thereof, e.g., sodium hyaluronate or potassium hyaluronate, heparan sulfate, and other disaccharides such as sucrose, lactulose, lactose, maltose, trehalose, cellobiose, mannobiose and chitobiose. Glycosaminoglycans can be purchased from Sigma, and many other biochemical suppliers.

In one embodiment, the first GAG is hyaluronic acid or a salt thereof and the second GAG is chondroitin sulfate. Hyaluronic acid is a well-known, naturally occurring, water soluble biodegradable polymer composed of two alternatively linked sugars, D-glucuronic acid and N-acetylglucosamine, linked via alternating $\beta$-(1,4) and $\beta$-(1,3) glycosidic bonds. Hyaluronic acid is a non-sulfated GAG. Hyaluronan. The polymer is hydrophilic and highly viscous in aqueous solution at relatively low solute concentrations. It often occurs naturally as the sodium salt, sodium hyaluronate. Methods of preparing commercially available hyaluronan and salts thereof are well known. Hyaluronan can be purchased from Seikagaku Company, Clear Solutions Biotech, Inc., Pharmacia Inc., Sigma Inc., and many other suppliers. Hyaluronic acid has one or more repeating units of the structure represented by the following formula:

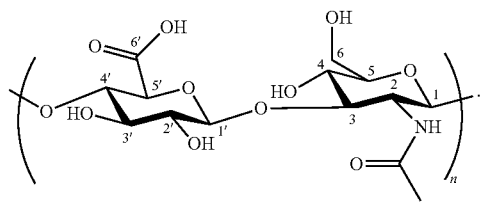

Accordingly, the repeating units in hyaluronic acid can be as follows:

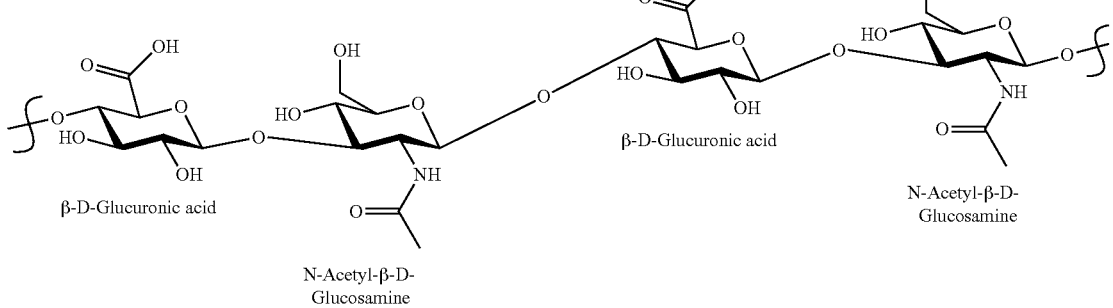

In general, hyaluronic acid or a salt thereof can have from about 2 to about 1,500,000 disaccharide units. In one embodiment, hyaluronic acid or a salt thereof can have a weight average molecular weight ranging from about 10,000 to about 3,000,000 Daltons (Da) in which the lower limit is from about 10,000, about 20,000, about 30,000, about 40,000, about 50,000, about 60,000, about 70,000, about 80,000, about 90,000, or about 100,000, and the upper limit is about 200,000, about 300,000, about 400,000, about 500,000, about 600,000, about 700,000, about 800,000, about 900,000, about 1,000,000, or about up to 2,800,000, where any of the lower limits can be combined with any of the upper limits.

Chondroitin sulfate is a linear sulfated polysaccharide composed of repeating β-D-glucuronic acid (GlcA) and N-acetyl-β-D-galactosamine (GalNAc) units arranged in the sequence by GlcA-β(1,3)-GalNAc-β(1,4) glycosidic bonds. In one embodiment, chondroitin sulfate has one or more repeating units of the structure represented by the following formula:

acts as a spacer between the first glycosaminoglycan and the second glycosaminoglycan. In general, the bi- or polyfunctional crosslinking agent comprises two or more functional groups capable of reacting with functional groups of the first glycosaminoglycan such as hyaluronic acid and the second glycosaminoglycan such as chondroitin sulfate, resulting in the formation of covalent bonds.

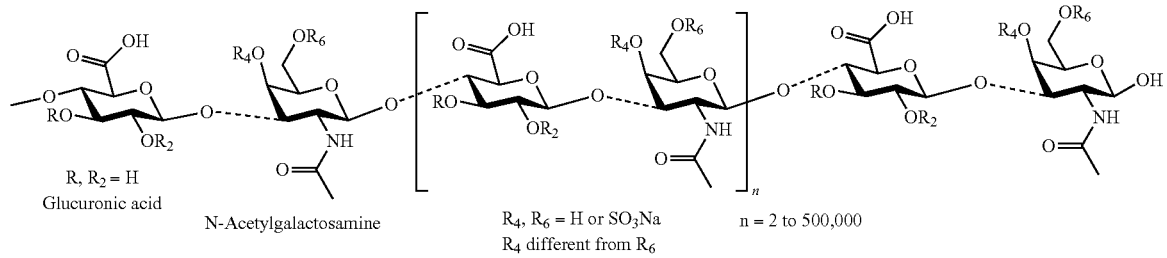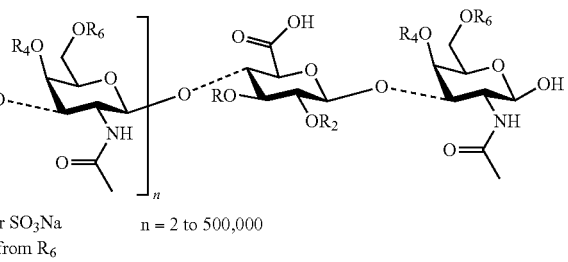

In one embodiment, chondroitin sulfate has one or more repeating units of the structure represented by the following formula:

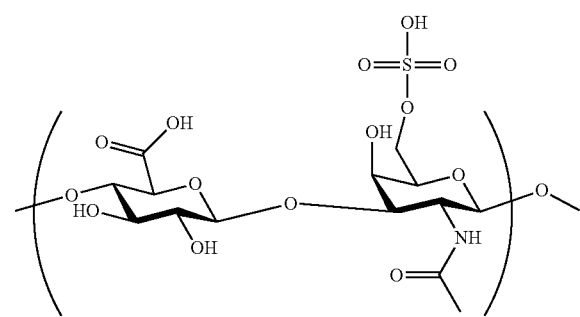

In general, chondroitin sulfate can have from about 2 to about 1,500,000 repeating units. In one embodiment, chondroitin sulfate can have a weight average molecular weight ranging from about 10,000 to about 3,000,000 Da in which the lower limit is from about 5,000, 10,000, about 20,000, about 30,000, about 40,000, about 50,000, about 60,000, about 70,000, about 80,000, about 90,000, or about 100,000, and the upper limit is about 200,000, about 300,000, about 400,000, about 500,000, about 600,000, about 700,000, about 800,000, about 900,000, about 1,000,000, or about 3,000,000 where any of the lower limits can be combined with any of the upper limits or any of the upper limits can be combined with any of the upper limits.

As discussed hereinabove, the reaction product includes one or more crosslinking agents, e.g., to crosslink the first glycosaminoglycan with the second glycosaminoglycan. The crosslinking agents for use herein can be any suitable crosslinking agent known in the art. In general, a suitable crosslinking agent is, for example, a crosslinking agent having complimentary functional groups to the first glycosaminoglycan such as hyaluronic acid and to the second glycosaminoglycan such as chondroitin sulfate. In one embodiment, a suitable crosslinking agent includes, for example, a bi- or polyfunctional crosslinking agent. The bi- or polyfunctional crosslinking agent connects the first glycosaminoglycan with the second glycosaminoglycan. In addition, the bi- or polyfunctional crosslinking agent further Suitable bi- or polyfunctional crosslinking agents include, for example, divinyl sulfone, diepoxides, multiepoxides, dihydrazides, dihydric alcohols, polyhydric alcohols, polyhydric thiols, anhydrides, carbodiimides, polycarboxylic acids, carboxymethyl thiols, cysteine, and cysteine-like amino acids and the like. In one embodiment, a bi- or polyfunctional crosslinking agent is a bis- or polyepoxide, such as diglycidyl ether derivatives. According to an embodiment, the bi- or polyfunctional epoxide crosslinking agent comprises two or more glycidyl ether functional groups. The glycidyl ether functional groups react with primary hydroxyl groups of the hyaluronic acid and the chondroitin sulfate, resulting in the formation of ether bonds. In one embodiment, suitable bis- or polyfunctional crosslinking agents include, for example, 1,4-butanediol diglycidyl ether (BDDE), 1,2-bis(2,3-epoxypropoxy)ethylene (EGDGE), ethylene glycol diglycidyl ether (EGDE), 1,2-ethanediol diglycidyl ether (EDDE), diepoxyoctane, 1,6-hexanediol diglycidyl ether, polypropylene glycol diglycidyl ether, polytetramethylene glycol diglycidyl ether, neopentyl glycol diglycidyl ether, polyglycerol polyglycidyl ester, diglycerol polyglycidyl ether, glycerol polyglycidyl ether, trimethylolpropane polyglycidyl ether, pentaerythritol polyglyglycidyl ether, sorbitol polyglycidyl ether, 1,2,7,8-diepoxyoctane, 1,3-butadiene diepoxide, pentaerythritol tetraglycidyl ether, polyepoxides and the like.

Suitable dihydrazide crosslinking agents include, for example, succinic acid dihydrazide, glutaric acid dihydrazide, adipic acid dihydrazide, pimelic acid dihydrazide, suberic acid dihydrazide, azalaic acid dihydrazide, sebacic acid dihydrazide, undecanedioic acid dihydrazide, dodecanedioic acid dihydrazide, brassylic acid dihydrazide, tetradecanedioic acid dihydrazide, pentadecanedioic acid dihydrazide, thapsic acid dihydrazide, octadecanedioic acid dihydrazide and the like.

Suitable dihydric alcohol crosslinking agents include, for example, ethylene glycol, propylene glycol, butylene glycol diethylene glycol, dipropylene glycol, neopentyl glycol, 1,3-propanediol, hexylene glycol, pentylene glycol, heptylene glycol, octylene glycol and the like. Suitable polyhydric alcohol crosslinking agents include, for example glycerin, pentaerythrite, xylitol, galactitol and the like. Suitable carbodiimide crosslinking agents include, for example, a compound of formula X—N=C=N—X, wherein each X independently is a $C_1$ to $C_6$ alkyl optionally substituted with 1-2 dialkylamino groups, or is a $C_5$ to $C_6$ cycloalkyl group, such as 1-ethyl-3-(3-dimethylaminopropyl) carbodiimide hydrochloride, and cyclohexyl carbodiimide. Suitable anhydride crosslinking agents include, for example, methacrylic anhydride, octeyl succinic anhydride and the like. In one embodiment, a suitable crosslinking agent is an aldehyde crosslinking agent such as, for example, formaldehyde, gluteraldehyde, gluraraldehyde and the like. In one embodiment, a suitable crosslinking agent includes, for example, an acid chloride, n-hydroxysuccinimide, polyethylene glycol diacrylates, polyethylene glycol diamines, ureas, diisocyanates and the like.

The crosslinked polymeric network of the present invention can be obtained by forming a solution of the first glycosaminoglycan and second glycosaminoglycan, and adding the foregoing one or more crosslinking agents. The solution is stirred for a suitable time sufficient to crosslink at least the first glycosaminoglycan with the second glycosaminoglycan. In one embodiment, crosslinking between the glycosaminoglycans can take place between 1° C. and about 99° C. over a time period of about 2 hours to about 24 hours.

The solution can contain a suitable solvent such as, for example, water, crown-ethers, dimethyl sulphoxide (DMSO), dimethyl formamide (DMF) and other aprotic solvents. In general, the amount of the first glycosaminoglycan can range from about 0.010 to about 50 wt. %, based on the total weight of the solution. In one embodiment, the amount of the first glycosaminoglycan can range from about 0.1 to about 5 wt. %, based on the total weight of the solution. In one embodiment, the amount of the second glycosaminoglycan can range from about 0.01 to about 50 wt. %, based on the total weight of the solution. In one embodiment, the amount of the second glycosaminoglycan can range from about 0.1 to about 5 wt. %, based on the total weight of the solution. The crosslinking agent can be added to the solution in an amount ranging from about 0.05 to about 10 wt. %, based on the total weight of the solution.

It will be readily understood and appreciated by those skilled in the art that the reaction product constitutes a complex mixture of compounds including, for example, the first glycosaminoglycan crosslinked with the second glycosaminoglycan, the first glycosaminoglycan crosslinked with the first glycosaminoglycan, the second glycosaminoglycan crosslinked with the second glycosaminoglycan, unreacted first glycosaminoglycan and unreacted second glycosaminoglycan. For example, in one illustrative embodiment, a first glycosaminoglycan crosslinked with a second glycosaminoglycan can have a weight average molecular weight ranging from about 20,000 to about 6,000,000 Da in which the lower limit is from about 20,000, about 30,000, about 40,000, about 50,000, about 60,000, about 70,000, about 80,000, about 90,000, or about 100,000 Da, and the upper limit is about 200,000, about 300,000, about 400,000, about 500,000, about 600,000, about 700,000, about 800,000, about 900,000, about 1,000,000, about 2,000,000, about 3,000,000, about 4,000,000, about 5,000,000 or up to about 6,000,000 Da where any of the lower limits can be combined with any of the upper limits. It is not necessary to isolate one or more specific components of the reaction product mixture. Indeed, the reaction product mixture can be employed as is.

In one embodiment, the crosslinked polymeric network of the present invention can be further crosslinked with one or more of the same or different third glycosaminoglycans. In general, the one or more third glycosaminoglycans can be any of the glycosaminoglycans discussed hereinabove. In one embodiment, the one or more third glycosaminoglycans are hyaluronic acid. In one embodiment, the one or more third glycosaminoglycans are chondroitin sulfate. In one embodiment, the one or more third glycosaminoglycans include hyaluronic acid and chondroitin sulfate.

The crosslinking agent for crosslinking the one or more of the same or different third glycosaminoglycans with the foregoing the crosslinked polymeric network can be any of the crosslinking agents discussed above. As one skilled in the art will understand, the crosslinking agent can the same crosslinking agent or a different crosslinking agent as the crosslinking agent used in the foregoing reaction product.

In general, the crosslinked polymeric network of the present invention can be further crosslinked with one or more of the same or different third glycosaminoglycans in substantially the same manner as discussed above.

In one embodiment, the crosslinked polymeric network of the present invention can be further mixed with one or more of the same or different third glycosaminoglycans. In general, the one or more third glycosaminoglycans can be any of the glycosaminoglycans discussed hereinabove. In one embodiment, the one or more third glycosaminoglycans are linear glycosaminoglycans. In one embodiment, the linear glycosaminoglycan is linear hyaluronic acid. In one embodiment, the linear glycosaminoglycan is linear chondroitin sulfate. In general, the one or more third glycosaminoglycans can be mixed with the crosslinked polymeric network of the present invention in an amount ranging from about 1 wt. % to about 20 wt. %, based on the total weight of the mixture. In one embodiment, the one or more third glycosaminoglycans can be mixed with the crosslinked polymeric network of the present invention in an amount ranging from about 1 wt. % to about 10 wt. %, based on the total weight of the mixture. In one embodiment, the one or more third glycosaminoglycans can be mixed with the crosslinked polymeric network of the present invention in an amount ranging from about 1 wt. % to about 5 wt. %, based on the total weight of the mixture.

In another embodiment of the present invention, a biomedical device is provided which comprise the crosslinked polymeric networks of the present invention at their surfaces. The crosslinked polymeric network may be provided over the entire surface of the biomedical device or over only a portion of the biomedical device surface. The crosslinked polymeric network may also be provided within the construct of the biomedical device. As used herein, the term "biomedical device" shall be understood to mean any article that is designed to be used while either in or on mammalian tissues or fluid, and preferably in or on human tissue or fluids. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses. The preferred biomedical devices are ophthalmic devices, particularly contact lenses, and most particularly contact lenses made from silicone hydrogels.

As used herein, the term "ophthalmic device" refers to devices that reside in or on the eye. These devices can provide optical correction, wound care, tissue repair, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts, viscoelastics and the like. As is understood by one skilled in the art, a lens is considered to be "soft" if it can be folded back upon itself without breaking.

The biomedical devices to be surface modified according to the present invention can be any material known in the art capable of forming a biomedical device as described above. In one embodiment, a biomedical device includes devices formed from material not hydrophilic per se. Such devices are formed from materials known in the art and include, by way of example, polysiloxanes, perfluoropolyethers, fluorinated poly(meth)acrylates or equivalent fluorinated polymers derived, e.g., from other polymerizable carboxylic acids, polyalkyl (meth)acrylates or equivalent alkylester polymers derived from other polymerizable carboxylic acids, or fluorinated polyolefins, such as fluorinated ethylene propylene polymers, or tetrafluoroethylene, preferably in combination with a dioxol, e.g., perfluoro-2,2-dimethyl-1, 3-dioxol. Representative examples of suitable bulk materials include, but are not limited to, Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to about 73 mol % of perfluoro-2, 2-dimethyl-1,3-dioxol and about 37 to about 27 mol % of tetrafluoroethylene, or of about 80 to about 90 mol % of perfluoro-2,2-dimethyl-1,3-dioxol and about 20 to about 10 mol % of tetrafluoroethylene.

In another embodiment, a biomedical device includes a device formed from material hydrophilic per se, since reactive groups, e.g., carboxy, carbamoyl, sulfate, sulfonate, phosphate, amine, ammonium or hydroxy groups, are inherently present in the material and therefore also at the surface of a biomedical device manufactured therefrom. Such devices are formed from materials known in the art and include, by way of example, polyhydroxyethyl acrylate, polyhydroxyethyl methacrylate, polyvinyl pyrrolidone (PVP), polyacrylic acid, polymethacrylic acid, polyacrylamide, polydimethylacrylamide (DMA), polyvinyl alcohol and the like and copolymers thereof, e.g., from two or more monomers selected from hydroxyethyl acrylate, hydroxyethyl methacrylate, N-vinyl pyrrolidone, acrylic acid, methacrylic acid, acrylamide, dimethyl acrylamide, vinyl alcohol and the like. Representative examples of suitable bulk materials include, but are not limited to, Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon, Atlafilcon and the like. Examples of other suitable bulk materials include Balafilcon A, Hilafilcon A, Alphafilcon A, Bilafilcon B and the like.

In another embodiment, a biomedical device to be surface modified according to the present invention include a device which is formed from material which are amphiphilic segmented copolymers containing at least one hydrophobic segment and at least one hydrophilic segment which are linked through a bond or a bridge member.

It is particularly useful to employ biocompatible materials herein including both soft and rigid materials commonly used for ophthalmic lenses, including contact lenses. In general, non-hydrogel materials are hydrophobic polymeric materials that do not contain water in their equilibrium state. Typical non-hydrogel materials comprise silicone acrylics, such as those formed bulky silicone monomer (e.g., tris (trimethylsiloxy)silylpropyl methacrylate, commonly known as "TRIS" monomer), methacrylate end-capped poly (dimethylsiloxane) prepolymer, or silicones having fluoroalkyl side groups (polysiloxanes are also commonly known as silicone polymers).

On the other hand, hydrogel materials comprise hydrated, crosslinked polymeric systems containing water in an equilibrium state. Hydrogel materials contain about 5 wt. % water or more (up to, for example, about 80 wt. %). The preferred hydrogel materials, include silicone hydrogel materials. In one preferred embodiment, materials include vinyl functionalized polydimethylsiloxanes copolymerized with hydrophilic monomers as well as fluorinated methacrylates and methacrylate functionalized fluorinated polyethylene oxides copolymerized with hydrophilic monomers. Representative examples of suitable materials for use herein include those disclosed in U.S. Pat. Nos. 5,310,779; 5,387, 662; 5,449,729; 5,512,205; 5,610,252; 5,616,757; 5,708, 094; 5,710,302; 5,714,557 and 5,908,906, the contents of which are incorporated by reference herein.

In one embodiment, hydrogel materials for biomedical devices, such as contact lenses, can contain a hydrophilic monomer such as one or more unsaturated carboxylic acids, vinyl lactams, amides, polymerizable amines, vinyl carbonates, vinyl carbamates, oxazolone monomers, copolymers thereof and the like and mixtures thereof. Useful amides include acrylamides such as N,N-dimethylacrylamide and N,N-dimethylmethacrylamide. Useful vinyl lactams include cyclic lactams such as N-vinyl-2-pyrrolidone. Examples of other hydrophilic monomers include hydrophilic prepolymers such as poly(alkene glycols) functionalized with polymerizable groups. Examples of useful functionalized poly(alkene glycols) include poly(diethylene glycols) of varying chain length containing monomethacrylate or dimethacrylate end caps. In a preferred embodiment, the poly (alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. In another embodiment, a hydrogel material can contain a siloxane-containing monomer and at least one of the aforementioned hydrophilic monomers and/or prepolymers.

Non-limited examples of hydrophobic monomers are $C_1$-$C_{20}$ alkyl and $C_3$-$C_{20}$ cycloalkyl (meth)acrylates, substituted and unsubstituted aryl (meth)acrylates (wherein the aryl group comprises 6 to 36 carbon atoms), (meth) acrylonitrile, styrene, lower alkyl styrene, lower alkyl vinyl ethers, and $C_2$-$C_{10}$ perfluoroalkyl (meth)acrylates and correspondingly partially fluorinate (meth)acrylates.

A wide variety of materials can be used herein, and silicone hydrogel contact lens materials are particularly preferred. Silicone hydrogels generally have a water content greater than about 5 wt. % and more commonly between about 10 to about 80 wt. %. Such materials are usually prepared by polymerizing a mixture containing at least one silicone-containing monomer and at least one hydrophilic monomer. Typically, either the silicone-containing monomer or the hydrophilic monomer functions as a crosslinking agent (a crosslinker being defined as a monomer having multiple polymerizable functionalities) or a separate crosslinker may be employed. Applicable silicone-containing monomers for use in the formation of silicone hydrogels are well known in the art and numerous examples are provided in U.S. Pat. Nos. 4,136,250; 4,153,641; 4,740,533; 5,034, 461; 5,070,215; 5,260,000; 5,310,779; and 5,358,995.

Representative examples of applicable silicone-containing monomers include bulky polysiloxanylalkyl(meth)

acrylic monomers. An example of a bulky polysiloxanylalkyl(meth)acrylic monomer is represented by the structure of Formula I:

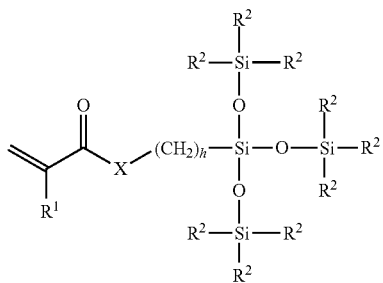
(I)

wherein X denotes —O— or —NR— wherein R denotes hydrogen or a $C_1$-$C_4$ alkyl; each $R^1$ independently denotes hydrogen or methyl; each $R^2$ independently denotes a lower alkyl radical, phenyl radical or a group represented by

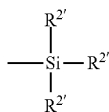

wherein each $R^{2'}$ independently denotes a lower alkyl or phenyl radical; and h is 1 to 10.

Representative examples of other applicable silicone-containing monomers include, but are not limited to, bulky polysiloxanylalkyl carbamate monomers as generally depicted in Formula Ia:

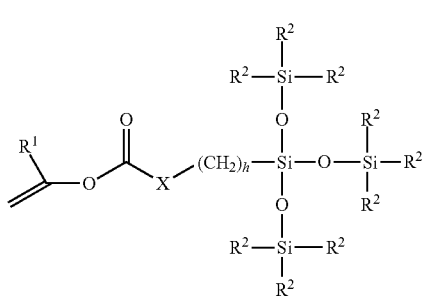
(Ia)

wherein X denotes —NR—; wherein R denotes hydrogen or a $C_1$-$C_4$ alkyl; $R^1$ denotes hydrogen or methyl; each $R^2$ independently denotes a lower alkyl radical, phenyl radical or a group represented by

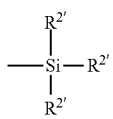

wherein each $R^{2'}$ independently denotes a lower alkyl or phenyl radical; and h is 1 to 10, and the like.

Examples of bulky monomers are 3-methacryloyloxypropyltris(trimethylsiloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like and mixtures thereof.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicone-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacrylates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulae II and III:

$$E(*D*A*D*G)_a*D*A*D*E'; \text{ or} \qquad (II)$$

$$E(*D*G*D*A)_a*D*A*D*E'; \text{ or} \qquad (III)$$

wherein:
D independently denotes an alkyl diradical, an alkyl cycloalkyl diradical, a cycloalkyl diradical, an aryl diradical or an alkylaryl diradical having 6 to about 30 carbon atoms;
G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;
* denotes a urethane or ureido linkage;
a is at least 1;
A independently denotes a divalent polymeric radical of Formula IV:

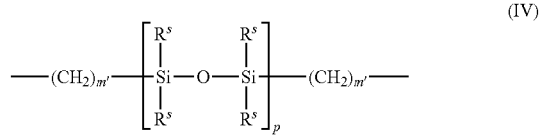
(IV)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;
each of E and E' independently denotes a polymerizable unsaturated organic radical represented by Formula V:

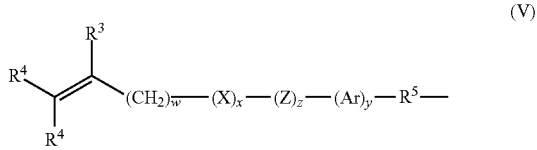

(V)

wherein:
- $R^3$ is hydrogen or methyl;
- $R^4$ is hydrogen, an alkyl radical having 1 to 6 carbon atoms, or a —CO—Y—$R^6$ radical wherein Y is —O—, —S— or —NH—;
- $R^5$ is a divalent alkylene radical having 1 to about 10 carbon atoms;
- $R^6$ is a alkyl radical having 1 to about 12 carbon atoms;
- X denotes —CO— or —OCO—;
- Z denotes —O— or —NH—;
- Ar denotes an aromatic radical having about 6 to about 30 carbon atoms;
- w is 0 to 6; x is 0 or 1; y is 0 or 1; and z is 0 or 1.

A preferred silicone-containing urethane monomer is represented by Formula VI:

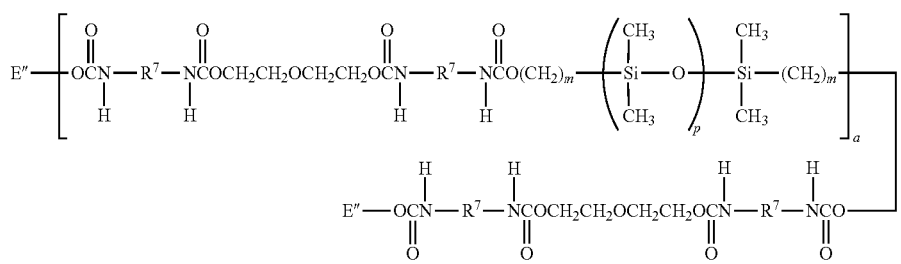

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E″ is a group represented by:

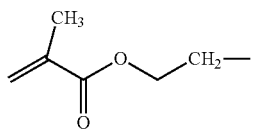

In another embodiment of the present invention, a silicone hydrogel material comprises (in bulk, that is, in the monomer mixture that is copolymerized) about 5 to about 50 percent, and preferably about 10 to about 25, by weight of one or more silicone macromonomers, about 5 to about 75 percent, and preferably about 30 to about 60 percent, by weight of one or more polysiloxanylalkyl (meth)acrylic monomers, and about 10 to about 50 percent, and preferably about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449, 729 and 5,512,205 are also useful substrates in accordance with the invention. The silane macromonomer may be a silicone-containing vinyl carbonate or vinyl carbamate or a polyurethane-polysiloxane having one or more hard-soft-hard blocks and end-capped with a hydrophilic monomer.

Another class of representative silicone-containing monomers includes fluorinated monomers. Such monomers have been used in the formation of fluorosilicone hydrogels to reduce the accumulation of deposits on contact lenses made therefrom, as disclosed in, for example, U.S. Pat. Nos. 4,954,587; 5,010,141; 5,079,319 and 7,994,356. Also, the use of silicone-containing monomers having certain fluorinated side groups, i.e., —($CF_2$)—H, have been found to improve compatibility between the hydrophilic and silicone-containing monomeric units. See, e.g., U.S. Pat. Nos. 5,321, 108 and 5,387,662.

The above silicone materials are merely exemplary, and other materials for use as substrates and have been disclosed in various publications and are being continuously developed for use in contact lenses and other medical devices can also be used. For example, a biomedical device can be formed from at least a cationic monomer such as cationic silicone-containing monomer or cationic fluorinated silicone-containing monomers.

Contact lenses for application of the present invention can be manufactured employing various conventional techniques, to yield a shaped article having the desired posterior and anterior lens surfaces. Spincasting methods are disclosed in U.S. Pat. Nos. 3,408,429 and 3,660,545; and static casting methods are disclosed in U.S. Pat. Nos. 4,113,224, 4,197,266 and 5,271,876. Curing of the monomeric mixture may be followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

Typically, an organic diluent is included in the initial monomeric mixture in order to minimize phase separation of polymerized products produced by polymerization of the monomeric mixture and to lower the glass transition temperature of the reacting polymeric mixture, which allows for a more efficient curing process and ultimately results in a more uniformly polymerized product. Sufficient uniformity of the initial monomeric mixture and the polymerized product is of particular importance for silicone hydrogels, primarily due to the inclusion of silicone-containing monomers which may tend to separate from the hydrophilic comonomer.

Suitable organic diluents include, for example, monohydric alcohols such as $C_6$-$C_{10}$ straight-chained aliphatic monohydric alcohols, e.g., n-hexanol and n-nonanol; diols such as ethylene glycol; polyols such as glycerin; ethers such as diethylene glycol monoethyl ether; ketones such as methyl ethyl ketone; esters such as methyl enanthate; and hydrocarbons such as toluene. Preferably, the organic diluent is sufficiently volatile to facilitate its removal from a cured article by evaporation at or near ambient pressure.

Generally, the diluent may be included at about 5 to about 60 percent by weight of the monomeric mixture, with about 10 to about 50 percent by weight being especially preferred. If necessary, the cured lens may be subjected to solvent removal, which can be accomplished by evaporation at or near ambient pressure or under vacuum. An elevated temperature can be employed to shorten the time necessary to evaporate the diluent.

Following removal of the organic diluent, the lens can then be subjected to mold release and optional machining operations. The machining step includes, for example, buffing or polishing a lens edge and/or surface. Generally, such machining processes may be performed before or after the article is released from a mold part. As an example, the lens may be dry released from the mold by employing vacuum tweezers to lift the lens from the mold.

As one skilled in the art will readily appreciate, biomedical device surface functional groups of the biomedical device according to the present invention may be inherently present at the surface of the device. However, if the biomedical device contains too few or no functional groups, the surface of the device can be modified by known techniques, for example, plasma chemical methods (see, for example, WO 94/06485), or conventional functionalization with groups such as —OH, or —$CO_2H$. Suitable biomedical device surface functional groups of the biomedical device include a wide variety of groups well known to the skilled artisan. Representative examples of such functional groups include, but are not limited to, hydroxy groups, cis 1,2-diols, cis 1,3-diols, α hydroxy acid groups (e.g., sialic acid, salicylic acid), carboxylic acids, di-carboxylic acids, catechols, silanols, silicates and the like.

In one embodiment, the foregoing biomedical devices are subjected to an oxidative surface treatment such as corona discharge or plasma oxidation followed by treatment with the crosslinked polymeric network of the present invention. For example, a biomedical device such as a silicone hydrogel formulation containing hydrophilic polymers, such as poly(N,N-dimethylacrylamide) or poly(N-vinylpyrrolidinone), is subjected to an oxidative surface treatment to form at least silicates on the surface of the lens and then the lens is treated with an aqueous solution containing the crosslinked polymeric network of the present invention to render a lubricious, stable, highly wettable crosslinked polymeric network based surface coating. The complexation treatment is advantageously performed under autoclave conditions (sterilization conditions).

The standard process such as a plasma process (also referred to as "electrical glow discharge processes") provides a thin, durable surface upon the biomedical device prior to binding the crosslinked polymeric network to at least a portion of the surface thereof. Examples of such plasma processes are provided in U.S. Pat. Nos. 4,143,949; 4,312,575; and 5,464,667.

Although plasma processes are generally well known in the art, a brief overview is provided below. Plasma surface treatments involve passing an electrical discharge through a gas at low pressure. The electrical discharge may be at radio frequency (typically 13.56 MHz), although microwave and other frequencies can be used. Electrical discharges produce ultraviolet (UV) radiation, in addition to being absorbed by atoms and molecules in their gas state, resulting in energetic electrons and ions, atoms (ground and excited states), molecules, and radicals. Thus, a plasma is a complex mixture of atoms and molecules in both ground and excited states, which reach a steady state after the discharge is begun. The circulating electrical field causes these excited atoms and molecules to collide with one another as well as the walls of the chamber and the surface of the material being treated.

The deposition of a coating from a plasma onto the surface of a material has been shown to be possible from high-energy plasmas without the assistance of sputtering (sputter-assisted deposition). Monomers can be deposited from the gas phase and polymerized in a low-pressure atmosphere (about 0.005 to about 5 torr, and preferably about 0.001 to about 1 torr) onto a substrate utilizing continuous or pulsed plasmas, suitably as high as about 1000 watts. A modulated plasma, for example, may be applied about 100 milliseconds on then off. In addition, liquid nitrogen cooling has been utilized to condense vapors out of the gas phase onto a substrate and subsequently use the plasma to chemically react these materials with the substrate. However, plasmas do not require the use of external cooling or heating to cause the deposition. Low or high wattage (e.g., about 5 to about 1000, and preferably about 20 to about 500 watts) plasmas can coat even the most chemical-resistant substrates, including silicones.

After initiation by a low energy discharge, collisions between energetic free electrons present in the plasma cause the formation of ions, excited molecules, and free-radicals. Such species, once formed, can react with themselves in the gas phase as well as with further ground-state molecules. The plasma treatment may be understood as an energy dependent process involving energetic gas molecules. For chemical reactions to take place at the surface of the lens, one needs the required species (element or molecule) in terms of charge state and particle energy. Radio frequency plasmas generally produce a distribution of energetic species. Typically, the "particle energy" refers to the average of the so-called Boltzman-style distribution of energy for the energetic species. In a low-density plasma, the electron energy distribution can be related by the ratio of the electric field strength sustaining the plasma to the discharge pressure (E/p). The plasma power density P is a function of the wattage, pressure, flow rates of gases, etc., as will be appreciated by the skilled artisan. Background information on plasma technology, hereby incorporated by reference, includes the following: A. T. Bell, Proc. Intl. Conf. Phenom. Ioniz. Gases, *"Chemical Reaction in Nonequilibrium Plasmas"*, 19-33 (1977); J. M. Tibbitt, R. Jensen, A. T. Bell, M. Shen, Macromolecules, "A Model for the Kinetics of Plasma Polymerization", 3, 648-653 (1977); J. M. Tibbitt, M. Shen, A. T. Bell, J. Macromol. Sci.-Chem., *"Structural Characterization of Plasma-Polymerized Hydrocarbons"*, A10, 1623-1648 (1976); C. P. Ho, H. Yasuda, J. Biomed, Mater. Res., *"Ultrathin coating of plasma polymer of methane applied on the surface of silicone contact lenses"*, 22, 919-937 (1988); H. Kobayashi, A. T. Bell, M. Shen, Macromolecules, *"Plasma Polymerization of Saturated and Unsaturated Hydrocarbons"*, 3, 277-283 (1974); R. Y. Chen, U.S. Pat. No. 4,143,949, Mar. 13, 1979, *"Process for Putting a Hydrophilic Coating on a Hydrophobic Contact lens"*; and H. Yasuda, H. C. Marsh, M. O. Bumgarner, N. Morosoff, J. of Appl. Poly. Sci., *"Polymerization of Organic*

*Compounds in an Electroless Glow Discharge. VI. Acetylene with Unusual Co-monomers"*, 19, 2845-2858 (1975).

Based on this previous work in the field of plasma technology, the effects of changing pressure and discharge power on the rate of plasma modification can be understood. The rate generally decreases as the pressure is increased. Thus, as pressure increases the value of E/p, the ratio of the electric field strength sustaining the plasma to the gas pressure decreases and causes a decrease in the average electron energy. The decrease in electron energy in turn causes a reduction in the rate coefficient of all electron-molecule collision processes. A further consequence of an increase in pressure is a decrease in electron density. Providing that the pressure is held constant, there should be a linear relationship between electron density and power.

In practice, contact lenses are surface-treated by placing them, in their unhydrated state, within an electric glow discharge reaction vessel (e.g., a vacuum chamber). Such reaction vessels are commercially available. The lenses may be supported within the vessel on an aluminum tray (which acts as an electrode) or with other support devices designed to adjust the position of the lenses. The use of a specialized support devices which permit the surface treatment of both sides of a lens are known in the art and may be used herein.

As mentioned above, the surface of the lens, for example, a silicone hydrogel continuous-wear lens is initially treated, e.g., oxidized, by the use of a plasma to render the subsequent crosslinked polymeric network surface deposition more adherent to the lens. Such a plasma treatment of the lens may be accomplished in an atmosphere composed of a suitable media, e.g., an oxidizing media such as oxygen, air, water, peroxide, $O_2$ (oxygen gas), etc., or appropriate combinations thereof, typically at an electric discharge frequency of about 13.56 Mhz, preferably between about 20 to about 500 watts at a pressure of about 0.1 to about 1.0 torr, preferably for about 10 seconds to about 10 minutes or more, more preferably about 1 to about 10 minutes. It is preferred that a relatively "strong" plasma is utilized in this step, for example, ambient air drawn through a five percent (5%) hydrogen peroxide solution. Those skilled in the art will know other methods of improving or promoting adhesion for bonding of the subsequent crosslinked polymeric network layer.

The biomedical device is then subjected to a surface treatment in accordance with the present invention. In general, the biomedical device such as a wettable silicone-based hydrogel lens is contacted with a solution containing at least one or more of crosslinked polymeric networks of the present invention, whereby the crosslinked polymeric network forms a complex with the plurality of biomedical device surface functional groups on the surface of the biomedical device. The biomedical devices can either be contacted with the solution containing at least the crosslinked polymeric networks directly in the mold assembly or the biomedical device can be released from the mold assembly and then contacted with the solution. The solutions can be water-based solutions containing the crosslinked polymeric networks and render a lubricious, stable, highly wettable surface. The complexation treatment is advantageously performed under autoclave conditions.

The solutions generally include compositions for direct instillation in the eye, including eye drop solutions and contact lens treating solutions distilled directly in the eye such as for rewetting a contact lens while worn as well as those that also qualify as a multi-purpose solution. Ophthalmic compositions also include compositions instilled indirectly in the eye, such as contact lens treating solutions for treating the contact lens prior to the lens being inserted on the eye or a packaging solution for storing the lens.

The ophthalmically acceptable solutions according to the present invention are physiologically compatible. Specifically, the compositions must be "ophthalmically safe" for use with a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe composition has a tonicity and pH that is compatible with the eye and comprises materials, and amounts thereof, that are non-cytotoxic according to ISO (International Standards Organization) standards and U.S. FDA regulations. The compositions should be sterile in that the absence of microbial contaminants in the product prior to release must be statistically demonstrated to the degree necessary for such products.

In general, the one or more of the crosslinked polymeric networks of the present invention can be present in the ophthalmic solution in an amount ranging from about 0.001 to about 10% w/w and preferably from about 0.1 to about 2% w/w. The ophthalmic solutions may be in the form of drops and are useful as a component of a contact lens cleaning, disinfecting or conditioning composition containing such materials. In one embodiment, the compositions and/or solutions of the present invention may be formulated as a "multi-purpose solution". A multi-purpose solution is useful for cleaning, disinfecting, storing, and rinsing a lens, particularly soft contact lenses. Multi-purpose solutions do not exclude the possibility that some wearers, for example, wearers particularly sensitive to chemical disinfectants or other chemical agents, may prefer to rinse or wet a contact lens with another solution, for example, a sterile saline solution prior to insertion of the lens. The term "multi-purpose solution" also does not exclude the possibility of periodic cleaners not used on a daily basis or supplemental cleaners for further removing proteins, for example, enzyme cleaners, which are typically used on a weekly basis. By the term "cleaning" is meant that the solution contains one or more agents in sufficient concentrations to loosen and remove loosely held lens deposits and other contaminants on the surface of a contact lens, which may be used in conjunction with digital manipulation (e.g., manual rubbing of the lens with a solution) or with an accessory device that agitates the solution in contact with the lens, for example, a mechanical cleaning aid.

Traditionally, multi-purpose solutions on the market have required a regimen involving mechanical rubbing of the lens with the multi-purpose solution, in order to provide the required disinfection and cleaning. Such a regimen is required under governmental regulatory authorities (e.g., the FDA or U.S. Food & Drug Administration (FDA)) for a Chemical Disinfection System that does not qualify as a Chemical Disinfecting Solution. In one embodiment of the present invention, it is possible to formulate a cleaning and disinfecting product that, on one hand, is able to provide improved cleaning and disinfection in the absence of a rubbing regimen and, on the other hand, is gentle enough to be used as a wetting agent, e.g., as an eye drop. For example, a product qualifying as a Chemical Disinfecting Solution must meet biocidal performance criteria established by the US FDA for Contact Lens Care Products (May 1, 1997) which criteria does not involve rubbing of the lenses. In one embodiment of the present invention, a composition is formulated to meet the requirements of the FDA or ISO Stand-Alone Procedure for contact lens disinfecting products. Similarly, the compositions of the present invention can be formulated to provide enhanced cleaning without the use of a rubbing regimen. Such formulations may ensure higher patient compliance and greater universal appeal than traditional multi-purpose disinfecting and cleaning products. A multi-purpose solution can have a viscosity of less than about 75 cps, or from about 1 to about 50 cps, or from about 1 to about 25 cps or at least about 95 percent weight by volume water in the total composition.

The aqueous ophthalmic solutions may contain, in addition to the one or more of the crosslinked polymeric networks of the present invention, one or more antimicrobial agents, preservatives and the like. The compositions generally include a primary antimicrobial agent. Antimicrobial agents suitable for use in the present invention include chemicals that derive their antimicrobial activity through a chemical or physiochemical interaction with the microbial organisms. These agents may be used alone or in combination.

water-soluble salts. In one embodiment, water-soluble polymeric biguanides for use herein can have a number average molecular weight of at least about 1,000 or a number average molecular weight from about 1,000 to about 50,000. Suitable water-soluble salts of the free bases include, but are not limited to, hydrochloride, borate, acetate, gluconate, sulfonate, tartrate and citrate salts. Generally, the hexamethylene biguanide polymers, also referred to as polyaminopropyl biguanide (PAPB), have number average molecular weights of up to about 100,000. Such compounds are known and are disclosed in U.S. Pat. No. 4,758,595 which is incorporated herein by reference.

PHMB is best described as a polymeric biguanide composition comprising at least three and preferably at least six biguanide polymers, which we refer to as PHMB-A, PHMB-CG and PHMB-CGA, the general chemical structures of which are depicted below.

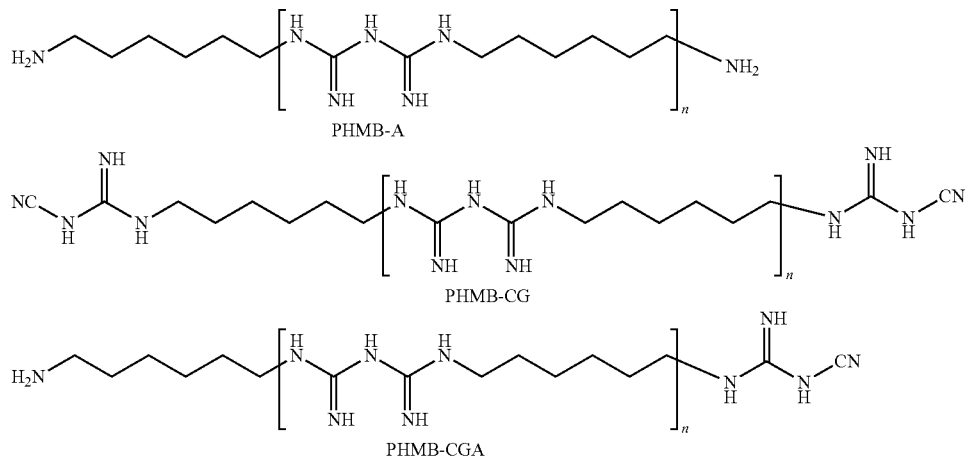

Suitable known ophthalmically acceptable antimicrobial agents include, but are not limited to, a biguanide or a salt or free base thereof, quaternary ammonium compound or a salt thereof or free base thereof; terpene or derivative thereof, a branched, glycerol monoalkyl ether, a branched, glycerol monoalkyl amine, a branched, glycerol monoalkyl sulphide, a fatty acid monoester, wherein the fatty acid monoester comprises an aliphatic fatty acid portion having six to fourteen carbon atoms, and an aliphatic hydroxyl portion, amidoamine compound, and the like and combinations thereof.

Suitable biguanide antimicrobial agents for use in the ophthalmic compositions can be any biguanide or salt thereof known in the art. Representative biguanides include non-polymeric biguanides, polymeric biguanides, salts thereof, free bases thereof and the like and mixtures thereof. Representative non-polymeric biguanides are the bis(biguanides), such as alexidine, chlorhexidine, salts of alexidine, e.g., alexidine HCl, salts of chlorhexidine, alexidine free base, and the like and mixtures thereof. The salts of alexidine and chlorhexidine can be either organic or inorganic and are typically disinfecting nitrates, acetates, phosphates, sulfates, halides and the like.

Representative polymeric biguanides include polymeric hexamethylene biguanides (PHMB) (commercially available from Zeneca, Wilmington, Del.), their polymers and For each of these polymers, "n" represents the average number of repeating groups. Actually, a distribution of polymer length would exist for each of the polymers shown. The prior synthetic routes to PHMB provided a polymeric biguanide composition with about 50% by weight of the polymeric composition as PHMB-CGA, that is, having a cyanoguanidino end cap on one end and an amine on the other end, about 25% by weight PHMB-A and about 25% by weight PHMB-CG. Given this approximate weight ratio of the three major PHMB polymers above, the percentage of cyanoguardino end caps is also about 50% of the total number of terminal groups. In this application we refer to this conventional polymeric biguanide composition as poly (hexamethylene biguanide) or PHMB.

A polymeric biguanide composition comprising less than 18 mole % of terminal amine groups as measured by $^{13}$CNMR can also be used. The polymeric biguanide composition can also be characterized by a relative increase in the molar concentration of terminal guanidine groups or terminal cyanoguardino groups. For example, in one embodiment, the biguanide composition comprises less than about 18 mole % of terminal amine groups and about 40 mol % or greater of terminal guanidine groups. In another embodiment, the biguanide composition comprises less than about 18 mole % of terminal amine groups and about 55 mol % or greater of terminal guanidine groups.

In this application, we refer to this biguanide composition as PHMB-CG*. We also refer to polymeric biguanide compositions in the generic sense as "hexamethylene biguanides", which one of ordinary skill in the art would recognize to include both PHMB as well as PHMB-CG*.

Representative examples of suitable quaternary ammonium compounds for use in the ophthalmic compositions of the present invention include, but are not limited to, poly[(dimethyliminio)-2-butene-1,4-diyl chloride] and [4-tris(2-hydroxyethyl)ammonio]-2-butenyl-w-[tris(2-hydroxyethyl) ammonio]-dichloride (chemical registry no. 75345-27-6) generally available as Polyquaternium 1 under the tradename ONAMER® M (Stepan Company, Northfield, Ill.), and the like and mixtures thereof.

Suitable terpene antimicrobial agents for use in the ophthalmic compositions of the present invention include any monoterpene, sesquiterpene and/or diterpene or derivatives thereof. Acyclic, monocyclic and/or bicyclic mono-, sesqui- and/or diterpenes, and those with higher numbers of rings, can be used. A "derivative" of a terpene as used herein shall be understood to mean a terpene hydrocarbon having one or more functional groups such as terpene alcohols, terpene ethers, terpene esters, terpene aldehydes, terpene ketones and the like and combinations thereof. Here, both the trans and also the cis isomers are suitable. The terpenes as well as the terpene moiety in the derivative can contain from 6 to about 100 carbon atoms and preferably from about 10 to about 25 carbon atoms.

Representative examples of suitable terpene alcohol antimicrobial agents include verbenol, transpinocarveol, cis-2-pinanol, nopol, isoborneol, carbeol, piperitol, thymol, α-terpineol, terpinen-4-ol, menthol, 1,8-terpin, dihydro-terpineol, nerol, geraniol, linalool, citronellol, hydroxycitronellol, 3,7-dimethyl octanol, dihydro-myrcenol, tetrahydro-alloocimenol, perillalcohol, falcarindiol and the like and mixtures thereof.

Representative examples of suitable terpene ether and terpene ester antimicrobial agents include 1,8-cineole, 1,4-cineole, isobornyl methylether, rose pyran, α-terpinyl methyl ether, menthofuran, trans-anethole, methyl chavicol, allocimene diepoxide, limonene mono-epoxide, isobornyl acetate, nonyl acetate, α-terpinyl acetate, linalyl acetate, geranyl acetate, citronellyl acetate, dihydro-terpinyl acetate, meryl acetate and the like and mixtures thereof.

Representative examples of terpene aldehyde and terpene ketone antimicrobial agents include myrtenal, campholenic aldehyde, perillaldehyde, citronellal, citral, hydroxy citronellal, camphor, verbenone, carvenone, dihydro-carvone, carvone, piperitone, menthone, geranyl acetone, pseudoionone, α-ionine, iso-pseudo-methyl ionone, n-pseudomethyl ionone, iso-methyl ionone, n-methyl ionone and the like and mixtures thereof. Any other terpene hydrocarbons having functional groups known in the art may be used herein in the inventive composition.

In one embodiment, suitable terpenes or derivatives thereof as antimicrobial agents include, but are not limited to, tricyclene, α-pinene, terpinolene, carveol, amyl alcohol, nerol, β-santalol, citral, pinene, nerol, b-ionone, caryophillen (from cloves), guaiol, anisaldehyde, cedrol, linalool, d-limonene (orange oil, lemon oil), longifolene, anisyl alcohol, patchouli alcohol, α-cadinene, 1,8-cineole, ρ-cymene, 3-carene, ρ-8-mentane, trans-menthone, borneol, α-fenchol, isoamyl acetate, terpin, cinnamic aldehyde, ionone, geraniol (from roses and other flowers), myrcene (from bayberry wax, oil of bay and verbena), nerol, citronellol, carvacrol, eugenol, carvone, α-terpineol, anethole, camphor, menthol, limonene, nerolidol, farnesol, phytol, carotene (vitamin $A_1$), squalene, thymol, tocotrienol, perillyl alcohol, borneol, simene, carene, terpenene, linalool, 1-terpene-4-ol, zingiberene (from ginger) and the like and mixtures thereof.

In one embodiment, the compound of component (ii) of the ophthalmic composition comprises a branched, glycerol monoalkyl ether. In another embodiment, the compound of component (ii) of the ophthalmic composition comprises a branched, glycerol monoalkyl amine. In another embodiment, the compound of component (ii) of the ophthalmic composition comprises a branched, glycerol monoalkyl sulphide. In still another embodiment, the compound of component (ii) of the ophthalmic composition comprises any one mixture of a branched, glycerol monoalkyl ether, a branched, glycerol monoalkyl amine or a branched, glycerol monoalkyl sulphide.

In one embodiment, the branched, glycerol monoalkyl ether for use in the ophthalmic compositions of the present invention is 3-[(2-ethylhexyl)oxy]-1,2-propanediol (EHOPD). In another embodiment, the branched, glycerol monoalkyl amine is 3-[(2-ethylhexyl)amino]-1,2-propanediol (EHAPD). In another embodiment, the branched, glycerol monoalkyl sulphide is 3-[(2-ethylhexyl)thio]-1,2-propanediol (EHSPD). In still another embodiment, the ophthalmic composition comprises any one mixture of EHOPD, EHAPD and EHSPD. The chemical structures of EHOPD, EHAPD and EHSPD are provided below.

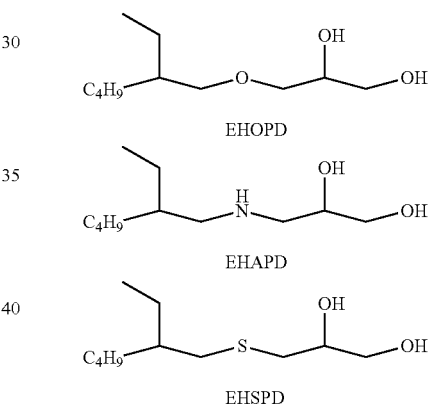

EHOPD is also referred to as octoxyglycerin and is sold under the tradename Sensiva® SC50 (Schülke & Mayr). EHOPD is a branched, glycerol monoalkyl ether known to be gentle to the skin, and to exhibit antimicrobial activity against a variety of Gram-positive bacteria such as *Micrococcus luteus, Corynebacterium aquaticum, Corynebacterium flavescens, Corynebacterium callunae*, and *Corynebacterium nephredi*. Accordingly, EHOPD is used in various skin deodorant preparations at concentrations between about 0.2 and 3 percent by weight. EHAPD can be prepared from 2-ethylhexylamine and 2,3-epoxy-1-propanediol using chemistry well known to those of ordinary skill in the art. EHSPD can be prepared from 2-ethylhexylthiol and 2,3-epoxy-1-propanediol using chemistry well known to those of ordinary skill in the art.

Suitable fatty acid monoester for use in the ophthalmic compositions of the present invention include those fatty acid monoesters comprising an aliphatic fatty acid portion having six to fourteen carbon atoms, and an aliphatic hydroxyl portion.

The term "aliphatic" refers to a straight or branched, saturated or unsaturated hydrocarbon having six to fourteen carbon atoms. In one embodiment, the aliphatic fatty acid portion is a straight chain, saturated or unsaturated hydrocarbon with eight to ten carbons. In another embodiment, the aliphatic fatty acid portion is a branched chain, saturated or unsaturated hydrocarbon with eight to ten carbons.

The aliphatic hydroxyl portion of the fatty acid monoester can be any aliphatic compound with at least one hydroxyl group. In many of the embodiments, the aliphatic hydroxyl portion will have from three to nine carbons. The aliphatic hydroxyl portion can include, but is not limited to, propylene glycol, glycerol, a polyalkylene glycol, e.g., polyethylene glycol or polypropylene glycol, a cyclic polyol, e.g., sorbitan, glucose, mannose, sucrose, fructose, fucose and inositol and derivatives thereof, and a linear polyol, e.g., mannitol and sorbitol and derivatives thereof and the like and mixtures thereof.

Representative examples of suitable amidoamines for use in the ophthalmic compositions of the present inventions include those amidoamines of the general formula: $R^{15}$—$(OCH_2CH_2)_m$—$X$—$(CH_2)_n$—$Y$ wherein $R^{15}$ is a is $C_6$-$C_{30}$ saturated or unsaturated hydrocarbon including by way of example, a straight or branched, substituted or unsubstituted alkyl, alkylaryl, or alkoxyaryl group; m is zero to 16; n is 2 to 16; X is —C(O)—$NR^{16}$— or —$R^{16}N$—(O)—; Y is —$N(R^{17})_2$ wherein each of $R^{16}$ and $R^{17}$ independently are hydrogen, a $C_1$-$C_8$ saturated or unsaturated alkyl or hydroxyalkyl, or a pharmaceutically acceptable salt thereof.

Some of the amidoamines utilized in the present invention are available from commercial sources. For example, myristamidopropyl dimethylamine is available from Alcon Inc. (Fort Worth, Tx.) under the tradename Aldox®; lauramidopropyl dimethylamine is available from Inolex Chemical Company (Philadelphia, Pa.) under the tradename LEXAMINE® L-13; and stearamidopropyl dimethylamine is also from Inolex Chemical Company as LEXAMINE® S-13. The above-described amidoamines can be synthesized in accordance with known techniques, including those described in U.S. Pat. No. 5,573,726.

The amount of the primary antimicrobial agent may vary depending on the specific agent employed. For the aforementioned organic nitrogen-containing agent, typically, such agents are present in concentrations ranging from about 0.00001 to about 0.5 wt. %, or from about 0.00003 to about 0.05 wt. %. For sorbic acid, higher amounts may be required, typically about 0.01 to about 1 wt. %, or from about 0.1 to about 0.5 wt. %. It is preferred that the antimicrobial agent is used in an amount that will at least partially reduce the microorganism population in the formulations employed. If desired, the antimicrobial agent may be employed in a disinfecting amount, which will reduce the microbial bioburden by at least two log orders in four hours and more preferably by one log order in one hour. Most preferably, a disinfecting amount is an amount which will eliminate the microbial burden on a contact lens when used in regimen for the recommended soaking time (FDA Chemical Disinfection Efficacy Test—July, 1985 Contact Lens Solution Draft Guidelines).

The aqueous solutions may further contain one or more other components that are commonly present in ophthalmic solutions, for example, surfactants, tonicity adjusting agents; buffering agents; chelating agents; pH adjusting agents, viscosity modifying agents, and demulcents and the like as discussed hereinabove, and which aid in making ophthalmic compositions more comfortable to the user and/or more effective for their intended use.

The pH of the solutions and/or compositions according to the present invention may be maintained within the range of pH of about 4.0 to about 9.0, or about 5.0 to about 8.0, or about 6.0 to about 8.0, or about 6.5 to about 7.8. In one embodiment, pH values of greater than or equal to about 7 at most.

In one embodiment, the biomedical device is transferred to an individual lens package containing a buffered saline solution containing at least one or more of the crosslinked polymeric networks of the present invention. Generally, a packaging system for the storage of an ophthalmic device according to the present invention includes at least a sealed container containing one or more unused ophthalmic devices immersed in an aqueous packaging solution. In one embodiment, the sealed container is a hermetically sealed blister-pack, in which a concave well containing an ophthalmic device such as a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

The amount of the one or more crosslinked polymeric networks employed in a packaging solution for storing an ophthalmic device in a packaging system of the present invention is an amount effective to improve the surface properties of the ophthalmic device. It is believed these crosslinked polymeric networks enhance initial and extended comfort when a contact lens, packaged in the solution and then removed from the packaging system, is placed on the eye for wearing. In one embodiment, the concentration of the one or more crosslinked polymeric networks in the packaging solution will range from about 0.01 to about 20% w/w. In one embodiment, the concentration of the one or more crosslinked polymeric networks present in the packaging solution will range from about 0.02 to about 0.1% w/w.

The packaging solutions according to the present invention are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations.

The packaging solution should also be sterile in that the absence of microbial contaminants in the product prior to release must be statistically demonstrated to the degree necessary for such products. The liquid media useful in the present invention are selected to have no substantial detrimental effect on the lens being treated or cared for and to allow or even facilitate the present lens treatment or treatments. In one embodiment, the liquid media is aqueous-based. A particularly useful aqueous liquid medium is that derived from saline, for example, a conventional saline solution or a conventional buffered saline solution.

The pH of the packaging solutions should be maintained within the range of about 6 to about 9, or from about 6.5 to about 7.8. Suitable buffers may be added, such as boric acid, sodium borate, potassium citrate, citric acid, sodium bicarbonate, TRIS and various mixed phosphate buffers (including combinations of $Na_2HPO_4$, $NaH_2PO_4$ and $KH_2PO_4$) and mixtures thereof. Generally, buffers will be used in amounts ranging from about 0.05 to about 2.5 percent by weight of the solution. In one embodiment, buffers will be used in amounts ranging from about 0.1 to about 1.5 percent by weight of the solution. In one embodiment, the packaging solutions of this invention will contain a borate buffer, e.g., a borate buffer containing one or more of boric acid, sodium borate, potassium tetraborate, potassium metaborate or mixtures thereof.

Typically, the packaging solutions are also adjusted with tonicity agents, to approximate the osmotic pressure of normal lacrimal fluids which is equivalent to a 0.9 percent solution of sodium chloride or 2.5 percent of glycerol solution. The packaging solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Suitable tonicity adjusting agents include, for example, sodium and potassium chloride, dextrose, glycerin, calcium and magnesium chloride and the like and mixtures thereof. These tonicity adjusting agents are typically used individually in amounts ranging from about 0.01 to about 2.5% w/v. In one embodiment, the tonicity adjusting agents are used in amounts ranging from about 0.2 to about 1.5% w/v. The tonicity agent will be employed in an amount to provide a final osmotic value of at least about 200 mOsm/kg. In one embodiment, the tonicity adjusting agents are used in an amount to provide a final osmotic value of from about 200 to about 400 mOsm/kg. In one embodiment, the tonicity adjusting agents are used in an amount to provide a final osmotic value of from about 250 to about 350 mOsm/kg. In one embodiment, the tonicity adjusting agents are used in an amount to provide a final osmotic value of from about 280 to about 320 mOsm/kg.

If desired, one or more additional components can be included in the packaging solution. Such additional component or components are chosen to impart or provide at least one beneficial or desired property to the packaging solution. In general, the additional components may be selected from components which are conventionally used in one or more ophthalmic device care compositions. Suitable additional components include, for example, cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Suitable sequestering agents include, for example, disodium ethylene diamine tetraacetate, alkali metal hexametaphosphate, citric acid, sodium citrate and the like and mixtures thereof.

Suitable viscosity builders include, for example, hydroxyethyl cellulose, hydroxymethyl cellulose, polyvinyl pyrrolidone, polyvinyl alcohol and the like and mixtures thereof.

Suitable antioxidants include, for example, sodium metabisulfite, sodium thiosulfate, N-acetylcysteine, butylated hydroxyanisole, butylated hydroxytoluene and the like and mixtures thereof.

The method of packaging and storing a biomedical device such as a contact lens according to the present invention includes at least packaging a biomedical device immersed in the aqueous packaging solution described above. The method may include immersing the biomedical device in an aqueous packaging solution prior to delivery to the customer/wearer, directly following manufacture of the contact lens. Alternately, the packaging and storing in the packaging solution may occur at an intermediate point before delivery to the ultimate customer (wearer) but following manufacture and transportation of the lens in a dry state, wherein the dry lens is hydrated by immersing the lens in the packaging solution. Consequently, a package for delivery to a customer may include a sealed container containing one or more unused contact lenses immersed in an aqueous packaging solution according to the present invention.

In one embodiment, the steps leading to the present ophthalmic device packaging system includes (1) molding a biomedical device in a mold comprising at least a first and second mold portion, (2) hydrating and cleaning the biomedical device in a container comprising at least one of the mold portions, (3) introducing the packaging solution with the one or more crosslinked polymeric networks into the container with the biomedical device supported therein, and (4) sealing the container. In one embodiment, the method also includes the step of sterilizing the contents of the container. Sterilization may take place prior to, or most conveniently after, sealing of the container and may be affected by any suitable method known in the art, e.g., by autoclaving of the sealed container at temperatures of about 120° C. or higher.

In another embodiment, the crosslinked polymeric network of the present invention can be in a gel formulation. As will be readily be understood by those skilled in the field of formulations, a gel is semisolid, suspension-type systems. Accordingly, in one embodiment, a gel formulation can include one or more of the crosslinked polymeric networks of the present invention and one or more gel forming agents. Gel forming agents for use herein can be any gelling agent typically used in the art for semi solid gel dosage forms. As used herein, the term "gelling agent" is intended to mean a compound used to render a liquid vehicle into a jelly-like vehicle. Exemplary gelling agents include, by way of example and without limitation, synthetic macromolecules, cellulose derivatives (e.g. carboxymethylcellulose and hydroxypropylmethyl-cellulose) and natural gums (e.g. tragacanth). The synthetic macromolecules include carbomers (e.g. Carbomer 910, 934, 934P, 940, 941, and 1342), which are high molecular weight water-soluble polymers of acrylic acid crosslinked with allyl ethers of sucrose and/or pentaerythritol. Carbomers have different viscosities depending on their polymeric composition. Gelling agents may be selected from any of synthetic or semi-synthetic polymeric materials, polyacrylate copolymers, cellulose derivatives and polymethyl vinyl ether/maleic anhydride copolymers. Various grades of Carbopol such as, for example, Carbopol 934, 940, 941, 974, 980, 981, 1342, 5984, ETD2020, ETD 2050, and Ultrez 10 (available from Noveon of Cleveland, Ohio) can be used in the present invention. The present invention preferably includes Carbopol 980 as a gelling agent. A Carbopol is a carbomer. Generally, carbomers are synthetic high molecular weight polymer of acrylic acid that are cross linked with either allylsucrose or allylethers of pentaerythritol.

The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. As a topical product, carbomer gels possess optimum rheological properties. The inherent pseudo plastic flow permits immediate recovery of viscosity when shear is terminated and the high yield value and quick break make it ideal for dispensing. In the present pharmaceutical formulations, carbomer gels are used as a suspending or viscosity increasing agent. Aqueous solution of Carbopol is acidic in nature due to the presence of free carboxylic acid residues. Neutralization of this solution crosslinks and gelatinizes the polymer to form a viscous integral structure of desired viscosity. The amount of gelling agents varies widely and will ordinarily range from about 0.1% to about 10% w/w.

The gel compositions can be incorporated into wound dressings (e.g., bandages, adhesive bandages, transdermal patches). Generally, in these embodiments, the gel compositions are embedded within puffs, gauzes, fleeces, gels, powders, sponges, or other materials that are associated with a second layer to form a wound dressing. Absorption enhancers can also be used to increase the flux of the composition, and particularly the therapeutic protein within the composition, across the skin. The rate of such flux can be controlled by either providing a rate controlling membrane or dispersing the therapeutic protein in a polymer matrix or gel.

In particular embodiments, the second layer of a wound dressing can be an elastomeric layer, vapor-permeable film, waterproof film, a woven or nonwoven fabric, mesh, or the like. The composition containing layer and second layer can be bonded using any suitable method (e.g., the application of adhesives, such as pressure sensitive adhesives, hot melt adhesives, curable adhesives; the application of heat or pressure, such as in lamination; a physical attachment through the use of stitching, studs, other fasteners; or the like).

Wound dressings may include adhesives for attachment to the skin or other tissue. Although any adhesive suitable for forming a bond with the skin or other tissue can be used, in certain embodiments a pressure sensitive adhesive is used. Pressure sensitive adhesives are generally defined as adhesives that adhere to a substrate when a light pressure is applied but leave little to no residue when removed. Pressure sensitive adhesives include solvent in solution adhesives, hot melt adhesives, aqueous emulsion adhesives, calenderable adhesives, and radiation curable adhesives.

The most commonly used elastomers in pressure sensitive adhesives can include natural rubbers, styrene-butadiene latexes, polyisobutylene, butyl rubbers, acrylics, and silicones. In particular embodiments, acrylic polymer or silicone-based pressure sensitive adhesives can be used. Acrylic polymers can often have a low level of allergenicity, be cleanly removable from skin, possess a low odor, and exhibit low rates of mechanical and chemical irritation. Medical grade silicone pressure sensitive adhesives can be chosen for their biocompatibility.

Amongst the factors that influence the suitability of a pressure sensitive adhesive for use in wound dressings of particular embodiments is the absence of skin irritating components, sufficient cohesive strength such that the adhesive can be cleanly removed from the skin, ability to accommodate skin movement without excessive mechanical skin irritation, and good resistance to body fluids.

The following examples are provided to enable one skilled in the art to practice the invention and are merely illustrative. The examples should not be read as limiting the scope of the invention as defined in the claims.

Example 1

Preparation of a crosslinked polymeric network of hyaluronic acid (HA) and chondroitin sulfate (CS) with 1,4-butanediol diglycidyl ether (BDDE) having the following general structure 1:

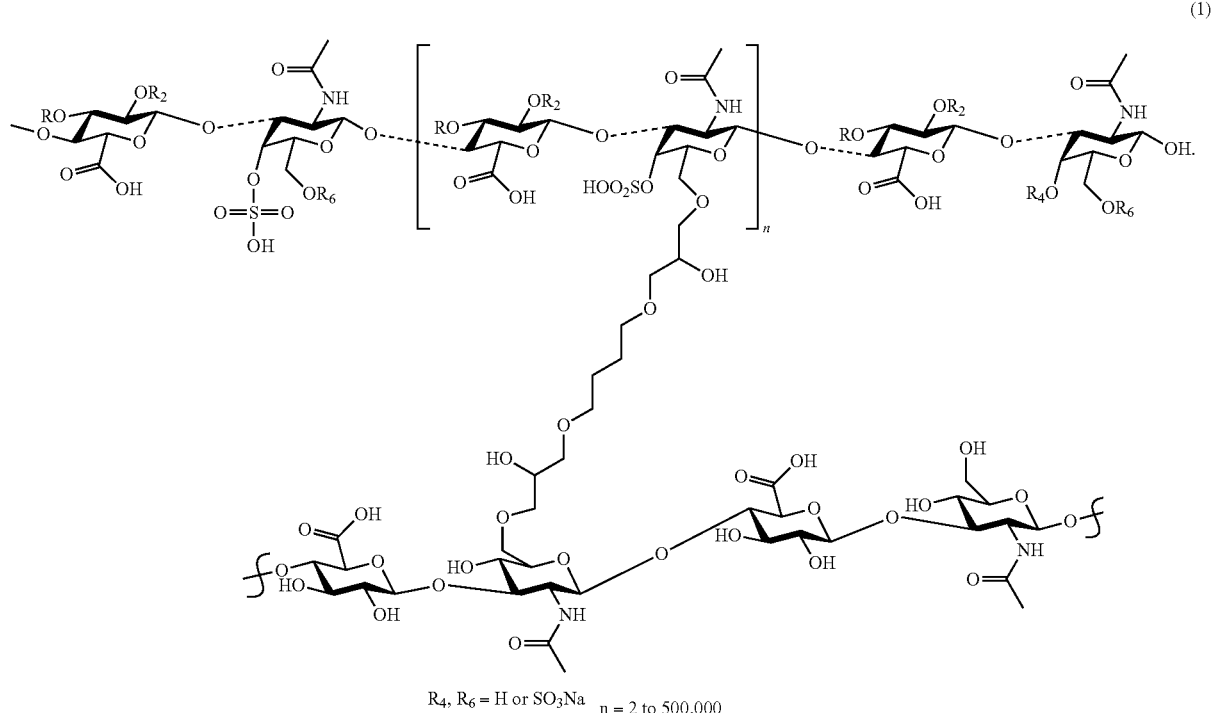

$R_4, R_6 = H$ or $SO_3Na$
$R_4$ different from $R_6$
$n = 2$ to $500,000$

To a 100 mL round bottom flask fitted with magnetic stirrer was added 60 mL of (reverse-osmosis) water and 3.00 g of HA (7.44 mmol based on disaccharide unit), and 3.00 g CS (6.01 mmol based on disaccharide unit). The solution was then stirred for 15 hours to ensure complete dissolution of materials to provide a clear solution having a pH of 6.65.

Example 2

Preparation of a crosslinked polymeric network of HA and CS with adipic acid dihydrazide (ADH) having the following structure 2:

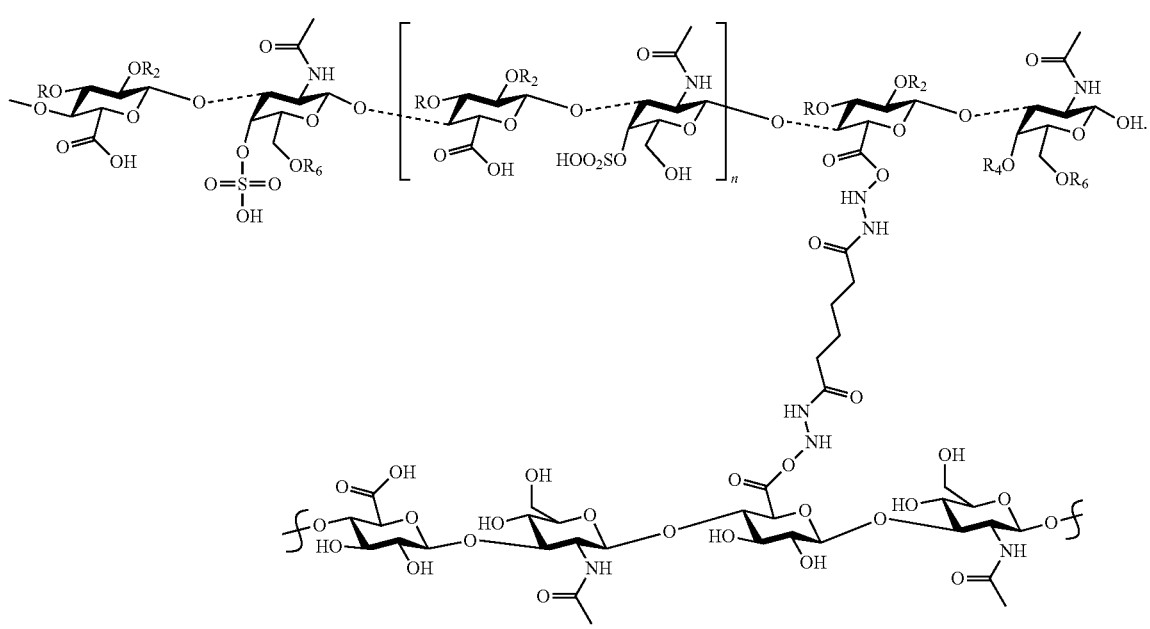

(2)

To this solution was added 1.2 mL of BDDE (6.25 mmol). After 15 minutes of stirring, the pH of the slightly hazy solution was adjusted to 8.5 with 0.2 g of a 10 wt. % solution of sodium hydroxide. After 24 hours the reaction mixture was then poured into 900 mL of ethanol to yield a precipitate and filtered. The solid was washed with 3×100 mL of ethanol and dried under high vacuum for 24 hours to yield 4.6 g (77% yield) of a white solid having the composition of HA, CS, branched and or crosslinked polymeric network of HA-CS, HA-HA, and CS-CS.

Analysis by size exclusion chromatography (SEC-MALS) of dialyzed material indicated a weight average molecular weight of 87,500 and a branching conformation slope of 0.375 as compared to the linear analog of 0.660. Integration by NMR of the inner methylene groups of the attached BDDE against the methyl groups of the acetamide indicate 2.90 mole % BDDE functionalized.

The SEC-MALS results of the crosslinked HA-CS structure 1 indicated an increase in the molecular weight (Absolute MW via Light Scattering Detection) as presented in Table 1 below.

TABLE 1

| | Mn (Daltons) | Mw (Daltons) | Mz (Daltons) | Polydispersity (PD) |
|---|---|---|---|---|
| HA | 21,200 | 34,000 | 47,400 | 1.60 |
| CS | 16,700 | 19,200 | 22,800 | 1.16 |
| HA-CS crosslinked | 31,170 | 88,940 | 53,610 | 2.85 |

In a 50 mL Erlenmeyer flask fitted with a stir bar was added 31.9 mL of (reverse-osmosis) water along with 1.50 g of HA, (3.72 mmol based on disaccharide unit). In a separate Erlenmeyer flask fitted with stir bar added 31.9 mL of (reverse-osmosis) water and 1.86 g of CS (3.72 mmol based on disaccharide unit). Both solutions were stirred for 15 hours to ensure complete dissolution of materials. To each solution was added 0.075 g, (0.389 mmol) of N-(3-Dimethylaminopropyl)-N'-ethylcarbodiimide hydrochloride in 0.5 mL of (reverse-osmosis) water. Each container was rinsed with 0.5 ml (reverse-osmosis) water. The solutions were allowed to stir for 5 minutes and then was added to a 100 mL round bottom flask fitted with stir bar. The flasks were rinsed with 2 mL each (reverse-osmosis) water. To this solution was added 0.062 g (0.353 mmol) of ADH in 0.5 ml of (reverse-osmosis) water.

The pH was adjusted from 7.08 to 4.54 with 6.08 g 1N HCl. After 40 minutes the pH was adjusted from 6.15 to 4.53 with 3.49 g 1N HCl. Next, after 6 hours the pH was at 4.65 and after 24 hours the pH was adjusted from 4.65 to 7.36 with 0.425 g of 10 wt. % sodium hydroxide. The solution was dialyzed using molecular weight cut-off (MWCO) 3500 in PBS buffer, (1.0 mM), along with 100 mM sodium chloride changing out the dialysis bath every 3 hours. A total of six exchanges were done. The third and fourth exchanges were in 50 mM NaCl and 1 mM PBS buffer. The last two exchanges being done in (reverse-osmosis) water only. A solution was lyophilized for 3 days to give 2.70 g of fluffy white solid, (78% yield) having the composition of HA, CS, branched and or crosslinked polymeric network of HA-CS, HA-HA, and CS-CS.

Analysis by size exclusion chromatography (SEC-MALS) of dialyzed material indicated a weight average molecular weight of 124,000 and a branching conformation slope of 0.445 as compared to the linear analog of 0.803. Integration by NMR of the inner methylene groups of the attached ADH against the methyl groups of the acetamide indicate 4.75 mole % ADH functionalized.

The SEC-MALS results of the crosslinked HA-CS structure 2 indicated an increase in the molecular weight (Absolute MW via Light Scattering Detection) as presented in Table 2 below.

TABLE 2

|  | Mn (Daltons) | Mw (Daltons) | Mz (Daltons) | Polydispersity (PD) |
|---|---|---|---|---|
| HA | 21,200 | 34,000 | 47,400 | 1.60 |
| CS | 16,700 | 19,200 | 22,800 | 1.16 |
| HA-CS crosslinked | 40,000 | 124,000 | 480,000 | 3.10 |

Example 3

Preparation of a linear HA mixed with a crosslinked polymeric network of HA and CS.

The crosslinked polymeric network of HA-CS of example 1 or 2 is further mixed with linear HA polymer chains of desired weight average molecular weight, i.e., about 10,000 to about 3,000,000 Da, to yield soft gels (crosslinked HA-CS with mixed HA chains) and then disintegrated using a high shear mixer, precipitated and dried. Alternatively, the crosslinked polymeric network of HA-CS of example 1 or 2 is mixed together with linear HA of desired weight average molecular weight in a wt. ratio of 1:1 to 1:20 (HA-CS:HA) and then dissolved in water to produce a gel for further use in various applications.

Example 4

A packaging solution is made by mixing the following components in the respective amounts listed in Table 3.

TABLE 3

| Ingredients | Parts |
|---|---|
| Trizma HCl | 0.627 |
| Trizma Base | 0.116 |
| Sodium Chloride | 0.577 |
| Purified Water, USP | 98.680 |
| Crosslinked HA-CS of Example 1 or 2 or 3 | 0.010 to 1.000 |
| pH | 3 to 6.2 |
| Osmolality | 200 to 400 |

Example 5

A packaging solution is made by mixing the following components in the respective amounts listed in Table 4.

TABLE 4

| Ingredients | Parts |
|---|---|
| Trizma HCl | 0.627 |
| Trizma Base | 0.116 |
| Sodium Chloride | 0.577 |
| Purified Water, USP | 98.680 |
| Crosslinked HA-CS of example 1 or 2 or 3 | 0.010 to 1.000 |
| Comfort Agents | 0.010 to 5.000 |

TABLE 4-continued

| Ingredients | Parts |
|---|---|
| pH | 3 to 6.2 |
| Osmolality | 200 to 400 |

Example 6

A packaging solution is made by mixing the following components in the respective amounts listed in Table 5.

TABLE 5

| Ingredients | Parts |
|---|---|
| Citric Acid, Anhydrous | 11.320 |
| Sodium Citrate | 62.220 |
| Sodium Chloride | 26.460 |
| Purified Water, USP | 100.000 |
| Crosslinked HA-CS of Example 1 or 2 or 3 | 0.010 to 1.000 |
| pH | 3 to 6.2 |
| Osmolality | 200 to 400 |

Example 7

A packaging solution is made by mixing the following components in the respective amounts listed in Table 6.

TABLE 6

| Ingredients | Parts |
|---|---|
| Citric Acid, Anhydrous | 11.320 |
| Sodium Citrate | 62.220 |
| Sodium Chloride | 26.460 |
| Purified Water, USP | 100.000 |
| Crosslinked HA_CS of example 1 or 2 or 3 | 0.010 to 1.000 |
| Comfort Agents | 0.010 to 5.000 |
| pH | 3.0 to 6.2 |
| Osmolality | 200 to 400 |

Example 8

A packaging solution is made by mixing the following components in the respective amounts listed in Table 7.

TABLE 7

| Ingredients | Parts |
|---|---|
| MOPS Sodium Salt | 0.560 |
| MOPS or 3-(N-morpholino)propanesulfonic acid | 0.520 |
| Sodium Chloride | 0.630 |
| Purified Water, USP | 98.280 |
| Crosslinked HA-CS of Example 1 or 2 or 3 | 0.010 to 1.000 |
| pH | 6.5 to 7.9 |
| Osmolality | 200 to 400 |

Example 9

A packaging solution is made by mixing the following components in the respective amounts listed in Table 8.

TABLE 8

| Ingredients | Parts |
| --- | --- |
| MOPS Sodium Salt | 0.560 |
| MOPS or 3-(N-morpholino)propanesulfonic acid | 0.520 |
| Sodium Chloride | 0.630 |
| Purified Water, USP | 98.280 |
| Crosslinked HA-CS of Example 1 or 2 or 3 | 0.010 to 1.000 |
| Comfort Agents | 0.010 to 5.000 |
| pH | 6.5 to 7.9 |
| Osmolality | 200 to 400 |

Example 10

A packaging solution is made by mixing the following components in the respective amounts listed in Table 9.

TABLE 9

| Ingredients | Parts |
| --- | --- |
| Monobasic sodium phosphate monohydrate | 0.015 |
| Dibasic sodium phosphate anhydrous | 0.065 |
| Sodium Chloride | 0.999 |
| Purified Water, USP | 99.040 |
| Crosslinked HA-CS of Example 1 or 2 or 3 | 0.010 to 1.000 |
| pH | 6.0 to 8 |
| Osmolality | 200 to 400 |

Example 11

A packaging solution is made by mixing the following components in the respective amounts listed in Table 10.

TABLE 10

| Ingredients | Parts |
| --- | --- |
| Monobasic sodium phosphate monohydrate | 0.015 |
| Dibasic sodium phosphate anhydrous | 0.065 |
| Sodium Chloride | 0.999 |
| Purified Water, USP | 99.040 |
| Crosslinked HA-CS of Example 1 or 2 or 3 | 0.010 to 1.000 |
| Comfort Agents | 0.010 to 5.000 |
| pH | 6.0 to 8 |
| Osmolality | 200 to 400 |

Example 12

A packaging solution is made by mixing the following components in the respective amounts listed in Table 11.

TABLE 11

| Ingredients | Parts |
| --- | --- |
| Sodium Borate | 0.610 |
| Boric Acid | 0.098 |
| Sodium Chloride | 0.886 |
| Purified Water, USP | 98.406 |
| Crosslinked HA-CS of Example 1 or 2 or 3 | 0.010 to 1.000 |
| pH | 7 to 9 |
| Osmolality | 200 to 400 |

Example 13

A packaging solution is made by mixing the following components in the respective amounts listed in Table 12.

TABLE 12

| Ingredients | Parts |
| --- | --- |
| Sodium Borate | 0.610 |
| Boric Acid | 0.098 |
| Sodium Chloride | 0.886 |
| Purified Water, USP | 98.406 |
| Crosslinked HA-CS of Example 1 or 2 or 3 | 0.010 to 1.000 |
| Comfort Agents | 0.010 to 5.000 |
| pH | 7 to 9 |
| Osmolality | 200 to 400 |

Example 14

Contact lenses made of Balafilcon A are cast and processed under standard manufacturing procedures. Balafilcon A is a copolymer comprised of 3-[tris(trimethylsiloxy)silyl] propyl vinyl carbamate, N-vinyl-2-pyrrolidone (NVP), 1,3-bis[4-vinyloxycarbonyloxy)but-1-yl]polydimethylsiloxane and N-vinyloxycarbonyl alanine. All Balafilcon A lenses are air-plasma treated prior to exposure to the crosslinked polymeric network.

For coating with the crosslinked polymeric network of Example 1, each lens is placed in a polypropylene blister package containing 3.8-mL of a 100 or 250 ppm (w/v) solution of the crosslinked polymeric network dissolved in an appropriate buffer system, e.g., aphosphate-buffered saline system (PBS), a borate-buffered saline (BBS) with or without containing 300 ppm EDTA. The blister packages are sealed with a foil lidstock and autoclaved at 121° C. for 30 minutes.

Example 15

Contact lenses made of Balafilcon A are cast and processed under standard manufacturing procedures. Balafilcon A is a copolymer comprised of 3-[tris(trimethylsiloxy)silyl] propyl vinyl carbamate, N-vinyl-2-pyrrolidone (NVP), 1,3-bis[4-vinyloxycarbonyloxy)but-1-yl]polydimethylsiloxane and N-vinyloxycarbonyl alanine. All Balafilcon A lenses are air-plasma treated prior to exposure to the crosslinked polymeric network.

For coating with the crosslinked polymeric network of Example 2, each lens is placed in a polypropylene blister package containing 3.8-mL of a 100 or 250 ppm (w/v) solution of the crosslinked polymeric network dissolved in an appropriate buffer system, e.g., a PBS, a BBS with or without containing 300 ppm EDTA. The blister packages are sealed with foil lidstock and autoclaved at 121° C. for 30 minutes.

It will be understood that various modifications may be made to the embodiments disclosed herein. Therefore, the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A method of preparing a package comprising a storable, sterile ophthalmic device, the method comprising:
    (a) immersing an unused ophthalmic device in an aqueous packaging solution comprising one or more crosslinked polymeric networks, wherein the one or more crosslinked polymeric networks comprise a reaction product of a first glycosaminoglycan, a second glycosaminoglycan, and a first crosslinking agent, wherein the first glycosaminoglycan is different than the second glycosaminoglycan, and wherein the aqueous packaging solution has an osmolality of at least about 180 mOsm/kg and a pH in the range of about 6 to about 9;
    (b) packaging the aqueous packaging solution and the unused ophthalmic device in a manner preventing contamination of the unused ophthalmic device by microorganisms; and
    (c) sterilizing the packaged aqueous packaging solution and unused ophthalmic device.

2. The method of claim 1, wherein the first glycosaminoglycan and the second glycosaminoglycan are independently selected from the group consisting of chondroitin, chondroitin sulfate, dermatan, dermatan sulfate, heparin, heparan sulfate, hyaluronan, and hyaluronic acid or a salt thereof.

3. The method of claim 1, wherein the first glycosaminoglycan is hyaluronic acid and the second glycosaminoglycan is chondroitin sulfate.

4. The method of claim 1, wherein the first crosslinking agent is a bi- or polyfunctional crosslinking agent comprising two or more functional groups capable of reacting with functional groups of the first glycosaminoglycan and the second glycosaminoglycan.

5. The method of claim 1, wherein the first crosslinking agent comprises a bis- or polyfunctional crosslinking agent selected from the group consisting of 1,4-butanediol diglycidyl ether (BDDE), 1,2-bis(2,3-epoxypropoxy)ethylene (EGDGE), ethylene glycol diglycidyl ether (EGDE), 1,2-ethanediol diglycidyl ether (EDDE), diepoxyoctane, 1,6-hexanediol diglycidyl ether, polypropylene glycol diglycidyl ether, polytetramethylene glycol diglycidyl ether, neopentyl glycol diglycidyl ether, polyglycerol polyglycidyl ester, diglycerol polyglycidyl ether, glycerol polyglycidyl ether, trimethylolpropane polyglycidyl ether, pentaerythritol polyglyglycidyl ether, sorbitol polyglycidyl ether, 1,2,7,8-diepoxyoctane, 1,3-butadiene diepoxide, pentaerythritol tetraglycidyl ether, and a polyepoxide.

6. The method of claim 1, wherein the reaction product comprises the first glycosaminoglycan crosslinked with the second glycosaminoglycan.

7. The method of claim 6, wherein the first glycosaminoglycan crosslinked with the second glycosaminoglycan has a weight average molecular weight ranging from about 20,000 to about 6,000,000 Da.

8. The method of claim 1, wherein the one or more crosslinked polymeric networks further comprise a reaction product of a mixture comprising (a) the reaction product of the first glycosaminoglycan, the second glycosaminoglycan, and the first crosslinking agent, and (b) one or more third glycosaminoglycans.

9. The method of claim 8, wherein the one or more third glycosaminoglycans are linear hyaluronic acid or linear chondroitin sulfate having a weight average molecular weight ranging from about 10,000 to about 3,000,000 Da.

10. The method of claim 8, wherein the mixture comprises from about 1 wt. % to about 20 wt. % of the one or more third glycosaminoglycans, based on the total weight of the mixture.

11. The method of claim 1, wherein the one or more crosslinked polymeric networks are present in the aqueous packaging solution in a concentration of from about 0.01 to about 20% w/w.

12. The method of claim 1, wherein the one or more crosslinked polymeric networks are present in the aqueous packaging solution in a concentration of from about 0.02 to about 0.1% w/w.

13. The method of claim 1, wherein the aqueous packaging solution further comprises one or more buffers.

14. The method of claim 13, wherein the one or more buffers comprise boric acid, sodium borate, potassium citrate, citric acid, sodium bicarbonate, TRIS, and a phosphate buffer.

15. The method of claim 1, wherein the aqueous packaging solution further comprises one or more tonicity agents.

16. The method of claim 15, wherein the one or more tonicity agents are present in the aqueous packaging solution in a concentration of from about 0.01 to about 2.5% w/v.

17. The method of claim 1, wherein the aqueous packaging solution further comprises one or more additional components.

18. The method of claim 17, wherein the one or more additional components comprise one or more cleaning agents, wetting agents, nutrient agents, sequestering agents, viscosity builders, contact lens conditioning agents, and antioxidants.

19. The method of claim 1, wherein the unused ophthalmic device is a contact lens.

20. The method of claim 1, wherein the first glycosaminoglycan is hyaluronic acid or a salt thereof having a weight average molecular weight ranging from about 10,000 to about 200,000, and the second glycosaminoglycan is chondroitin sulfate having a weight average molecular weight ranging from about 10,000 to about 100,000.

* * * * *